(12) United States Patent
Zhan

(10) Patent No.: US 8,592,618 B2
(45) Date of Patent: Nov. 26, 2013

(54) HIGHLY ACTIVE METATHESIS CATALYSTS SELECTIVE FOR ROMP AND RCM REACTIONS

(75) Inventor: Zheng-Yun James Zhan, Shanghai (CN)

(73) Assignee: Zannan Scitech Co., Ltd., Shanghai (CN)

( * ) Notice: Subject to any disclaimer, the term of this patent is extended or adjusted under 35 U.S.C. 154(b) by 590 days.

(21) Appl. No.: 12/684,410

(22) Filed: Jan. 8, 2010

(65) Prior Publication Data

US 2011/0172381 A1 Jul. 14, 2011

(51) Int. Cl.
  *C08F 4/78* (2006.01)
  *C08F 4/80* (2006.01)
  *B01J 23/46* (2006.01)
  *B01J 23/30* (2006.01)
  *C07F 15/00* (2006.01)

(52) U.S. Cl.
  USPC ............. 556/136; 556/57; 502/100; 526/172; 526/280; 526/281; 526/308

(58) Field of Classification Search
  USPC ............. 556/136, 137, 58, 57, 61; 526/169.1, 526/169, 172; 502/100
  See application file for complete search history.

(56) References Cited

U.S. PATENT DOCUMENTS

| | | | | |
|---|---|---|---|---|
| 6,867,303 | B2* | 3/2005 | Grela | 548/101 |
| 7,939,668 | B2* | 5/2011 | Puentener et al. | 548/103 |
| 2007/0043180 | A1* | 2/2007 | Zhan | 526/90 |
| 2010/0113795 | A1* | 5/2010 | Arlt et al. | 548/103 |

FOREIGN PATENT DOCUMENTS

| | | | | |
|---|---|---|---|---|
| DE | 10 2006 043 704 A1 * | 3/2008 | | C07F 15/00 |
| DE | 10 2007 018 148 A1 * | 10/2008 | | C07B 37/10 |
| EP | 1 905 777 A1 * | 11/2007 | | C07F 15/00 |
| WO | WO 2007/081987 A1 * | 7/2007 | | |
| WO | WO 2009/124853 A1 * | 10/2009 | | C07C 235/06 |

OTHER PUBLICATIONS

Yang et al., Chemistry—A European Journal, 2004, 10, 5761-5770.*
Slugovc et al. Organometallics, 2005, 24, 2255-2258.*
Varray et al. Organometallics 2003, 22, 2426-2435.*
Chen et al. Tetrahedron 2009, 65, 3397-3403.*
U.S. Appl. No. 13/075,564, filed Mar. 30, 2011, Zhan.

* cited by examiner

*Primary Examiner* — Rip A. Lee
(74) *Attorney, Agent, or Firm* — Oblon, Spivak, McClelland, Maier & Neustadt, L.L.P.

(57) ABSTRACT

The present invention relates to a kind of novel carbene ligands and ruthenium catalysts, which is highly active and selective for ROMP and RCM reactions, respectively. It discloses the significant electronic and steric effect of different substituted carbene ligands on the catalytic activity and stability of corresponding carbene ruthenium complexes; some of novel ruthenium complexes in the invention can be broadly used as catalysts highly effectively and selective for ROMP and RCM reactions. The invention also relates to preparation of new ruthenium catalysts and the uses in metathesis. Moreover, the invention also provides effective methods of making various functional polymers by ROMP reaction in the presence of new ruthenium catalysts.

17 Claims, 1 Drawing Sheet

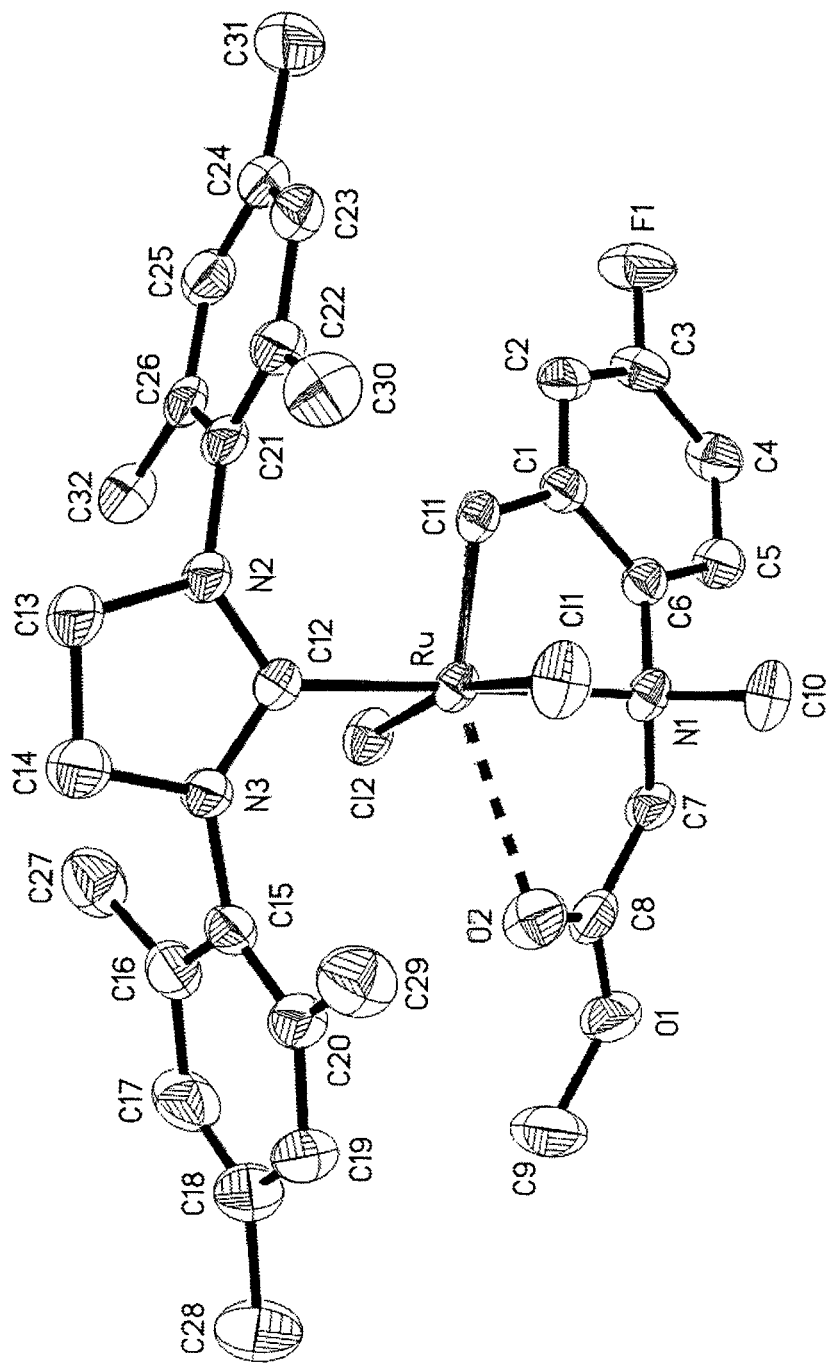

HIGHLY ACTIVE METATHESIS CATALYSTS SELECTIVE FOR ROMP AND RCM REACTIONS

FIELD OF THE INVENTION

The present invention relates to novel carbene ligands and their incorporated ruthenium catalysts, which are highly active and selective for different kinds of olefin metathesis reactions. The invention also relates to preparation of new ruthenium complexes and the use thereof in metathesis, especially effective for preparation of various functional polymers by ROMP reaction.

BACKGROUND OF THE INVENTION

Since Richard R. Schrock and Robert H. Grubbs prepared two kinds of metathesis catalysts with transition metal carbene structure in the 1990's, it has been drawn extensive attention in the development of more active and selective ruthenium catalysts for different kinds of olefin metathesis reactions, e.g., ring-opening metathesis polymerization (ROMP), ring-closing metathesis (RCM), and cross metathesis (CM).

So far, some ruthenium complexes have been reported as active metathesis catalysts (1a-1b and 2a-2f in Scheme 1) for RCM and ROMP reactions (References for listed catalysts in Scheme 1; 1a: Grubbs et al., *J. Am. Chem. Soc.* 1992, 114, 3974-3975; 1b: Grubbs et al., *Org. Lett* 1999, 1, 953-956; 2a: Hoveyda et al., *J. Am. Chem. Soc.* 1999, 121, 791-799 and WO200214376A2; 2b: Zhan et al., US20070043180A1 and WO 2007003135A1; 2c: Tupy et al., WO2007081987A2; 2d: Slugovc et al., *Organometallics* 2004, 23(15), 3623-3626; 2e: Slugovc et al., *Organometallics* 2005, 24(10), 2255-2258; 2f: Grela et al., WO2004035596A1). However, a disadvantage of all reported ruthenium catalysts is obviously substrate-dependent for different kinds of ruthenium catalysts in metathesis reactions, and it is still very difficult to find some active metathesis catalysts selective for RCM and ROMP reactions, respectively. Moreover, only a few metathesis catalysts such as Grubbs catalyst 1b could be used effectively to make high-strength and high-stiffness polydicyclopentadiene (PD-CPD) material by ROMP reaction.

Scheme 1: Structure of Some Ru Catalysts for ROMP and RCM Reaction

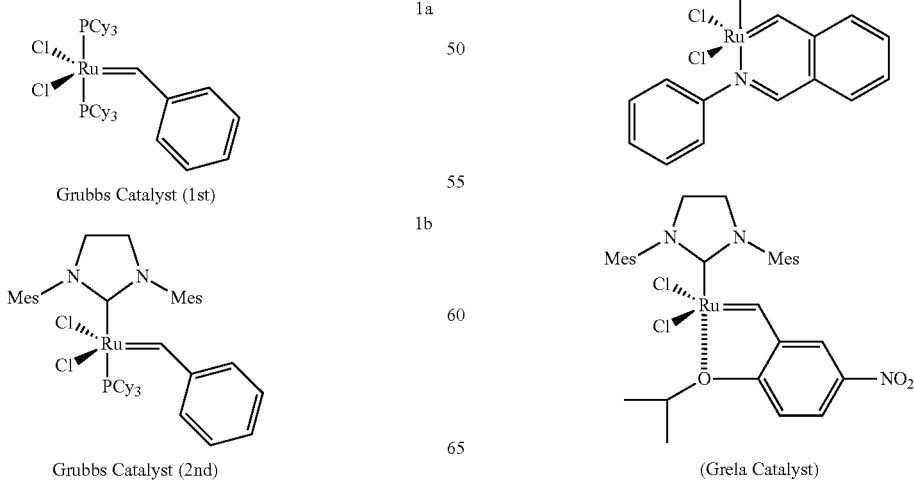

Scheme 1: Structure of Some Ru Catalysts for ROMP and RCM Reaction

Currently, ROMP reaction is broadly used for preparation of various high-strength and other functional polymers. To overcome the activity and selectivity problems for ROMP catalysts, it has become a goal to develop more active and selective metathesis catalysts as an alternative for ROMP and RCM reactions, especially in ROMP for effective preparation and modification of different functional polymer materials. It is significantly important to develop more active and selective ruthenium catalyst for ROMP reactions with different kinds of olefin substrates to prepare highly functional polymer materials and also to improve polymer properties.

SUMMARY OF THE INVENTION

The present invention relates to two classes of novel carbene ligands and their incorporated ruthenium complexes that can be used as highly active metathesis catalysts selective for RCM, CM, and ROMP reactions, respectively. The novel metathesis catalysts are ruthenium complexes with different kinds of new functionally substituted carbene ligands. The new ruthenium complexes of the invention can catalyze different kinds of metathesis reactions in a very effective manner and offer great advantage in activity and selectivity for different kinds of metathesis reactions, especially in ROMP effective for preparation of some functional polymer materials with unique chemical and physical properties. The novel ruthenium complexes of the invention have broad uses in the polymeric and pharmaceutical industries. Thus, the present invention comprises novel Ru complexes of the following formulas Ia and Ib, which has been evaluated to be highly active and selective for ROMP and RCM reactions with various olefin substrates and can be broadly used as an alternative to the previously reported catalysts.

In the first aspect, the present invention provides a kind of transition metal complex having the following structure Ia and Ib:

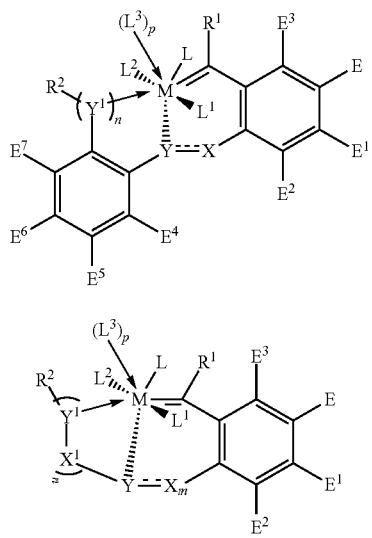

wherein:
m=0 or 1, and n=0 or 1;
When n=0; p=0 or 1; when n=1, p=0;
M is a transition metal;

$L^1$ and $L^2$ are the same or different and each selected from halide anion, $RC(O)O^-$ or $ArO^-$ anion;

L is an electron-donating ligand;

when m=1, X is oxygen, nitrogen, sulfur, CH, $CH_2$, carbonyl; Y is nitrogen, oxygen, CH, $CH_2$, imino, alkoxy, aryl, aryloxy, heteroaryl, alkylcarbonyl, alkoxycarbonyl, arylcarbonyl, aryloxycarbonyl, alkylimino, alkylamino, arylamino or heterocyclic amino group; "Y═X" is either single bond or double bond;

when m=0, Y is oxygen, nitrogen, carbonyl, imino, alkoxy, aryloxy, heterocyclic aryl, alkoxycarbonyl, aryloxycarbonyl, alkylimino, alkylamino, arylamino or heterocyclic amino group;

when n=0 and p=1, $L^3$ is an electron-donating ligand;

when n=1 and p=0, $X^1$ and $Y^1$ each is oxygen, nitrogen, sulfur, carbonyl, imino, CH, $CH_2$, alkyl, aryl, aryloxy, heterocyclic aryl, alkylamino, arylamino or heterocyclic amino group;

$R^1$ is H, alkyl, alkenyl, aryl, arylenyl, alkoxy, alkylthio, arylthio, aryloxy, heteroaryl or heterocyclic group;

$R^2$ is H, alkyl, aryl, alkylcarbonyl, arylcarbonyl, alkyoxycarbonyl, aryloxy-carbonyl, aminocarbonyl, heteroaryl or heterocyclic group;

E, $E^1$, $E^2$, $E^3$, $E^4$, $E^5$, $E^6$ and $E^7$ each is independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, amino, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom or heterocyclic group.

In one preferred embodiment Ia or Ib, wherein L is heterocyclic carbene ligand or phosphine $P(R^8)_2(R^9)$ having the following structure IIa, IIb, IIc or IId:

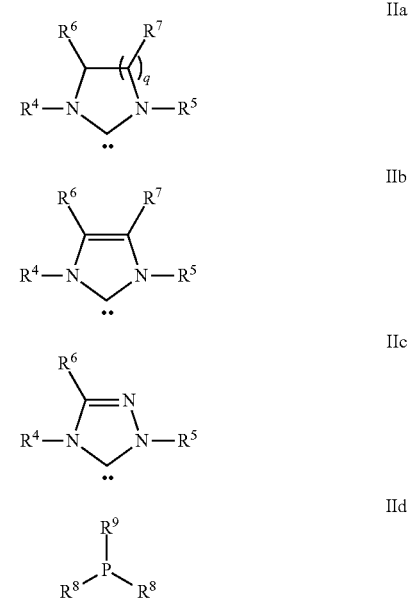

wherein:
q=1 or 2;
$R^4$ and $R^5$ each is alkyl, aryl, alkylamido, arylamido, heteroaryl or heterocyclic group;

$R^6$ and $R^7$ each is H, halogen atom, nitro, amino, alkyl, alkoxy, alkylthio, alkenyloxy, alkylsilyloxy, aryl, aryloxy, alkylcarbonyl, arylcarbonyl, alkoxycarbonyl, aryloxycarbonyl, amino, alkylaminocarbonyl, arylaminocarbonyl, alkylamido, arylamido, alkylaminosulfonyl, arylaminosulfonyl, sulfonylamido, heteroaryl or heterocyclic group;

$R^8$ and $R^9$ each is alkyl, alkoxy, aryl, aryloxy, heteroaryl or heterocyclic group.

In one more preferred embodiment of the present invention, wherein the structure IIa or IIb:

M is Ru,

L is $PCy_3$ (Cy=cyclohexyl) or N-heterocyclic ring ($H_2IMes$);

$L^1$ and $L^2$ each is chloride anion;

$R^1$ is H;

m=0 or 1, and n=1;

when m=0, Y is $CH_2$, NH, $C_1$-$C_{12}$ alkoxy, $C_1$-$C_{12}$ alkylamino or $C_6$-$C_{12}$ arylamino group;

when m=1, X is nitrogen, $C_1$-$C_{12}$ alkylamino, CH, $CH_2$, or carbonyl; Y is oxygen, nitrogen, imino, NH, $C_1$-$C_{12}$ alkyl, $C_1$-$C_{12}$ alkoxy, $C_1$-$C_{12}$ alkylamino, or $C_6$-$C_{12}$ arylamino; "$=$ X" is either single bond or double bond;

when n=1, $X^1$ is $CH_2$, substituted or unsubstituted phenyl, or carbonyl; $Y^1$ is oxygen or carbonyl;

when n=1, $R^2$ is methyl, ethyl, or isopropyl; when n=0, $R^2$ is H, halogen, $C_1$-$C_{12}$ alkyl or $C_1$-$C_{12}$ alkoxy in structure IIa.

E is H, halogen, nitro, $C_1$-$C_{12}$ alkyl, $C_1$-$C_{12}$ alkoxy, $C_1$-$C_{12}$ alkoxycarbonyl, $C_1$-$C_{12}$ alkylaminosulfonyl, $C_6$-$C_{12}$ arylaminosulfonyl;

$E^1$ and $E^2$ each is H, halogen, $C_1$-$C_{12}$ alkyl or $C_1$-$C_{12}$ alkoxy;

$E^3$ is H;

$E^4$ is H or $C_1$-$C_{12}$ alkyl;

$E^5$ and $E^6$ each is H, halogen, $C_1$-$C_{12}$ alkyl or $C_1$-$C_{12}$ alkoxy;

$E^7$ is H or $C_1$-$C_{12}$ alkyl.

Details of the invention are set forth in the description of the new ligand synthesis and complex preparation below. The objects and advantages of the present invention will be apparent from the following detailed description.

BRIEF DESCRIPTION OF THE DRAWINGS

FIG. 1: Single-crystal X-ray structure of a new Ru catalyst 8m (Ib).

DETAILED DESCRIPTION OF THE INVENTION

The present invention comprises two classes of novel carbene ligands and ruthenium complexes as catalysts more active and selective for ROMP reactions than prior reported metathesis catalysts and more effective for olefin ROMP reactions to prepare better quality of various functional polymer materials. Moreover, the high quality of the high strength PDCPD polymer has been prepared by ROMP reaction of raw material DCPD with one or more active ROMP catalysts developed in the invention.

The metathesis catalysts of the present invention comprise two kinds of novel ruthenium complexes having the structure of Formula Ia and Ib, and their broad uses effective for preparation of functional polymer materials by selective ROMP reaction, and the novel metathesis catalysts (0.1-0.002 mol %) could carry out ROMP reaction for a variety of cyclic olefin materials in high yield.

Synthesis of New Multi-Substituted Benzylidene Ligands and Ruthenium Complexes:

According to previously reported references and our developed synthetic methods, different kinds of new carbene ligands and ruthenium complexes having the structure of Formula Ia-Ib can be prepared based on three of alternative synthetic methods in the following Schemes 2-4, respectively. In Scheme 2, it was reported by M. Yamaguchi et al (*Chem. Commun.* 1998, 1399-1400) to carry out ortho-vinylation reaction regioselectively with ethyne and different kinds of substituted aminobenzene SM-1 to offer diversity of substituted 2-aminostyrene ligands (V), followed by reaction with a Ru complex (1a or 1b) to form the desired Ru complex Ia or Ib as follows:

Scheme 2:

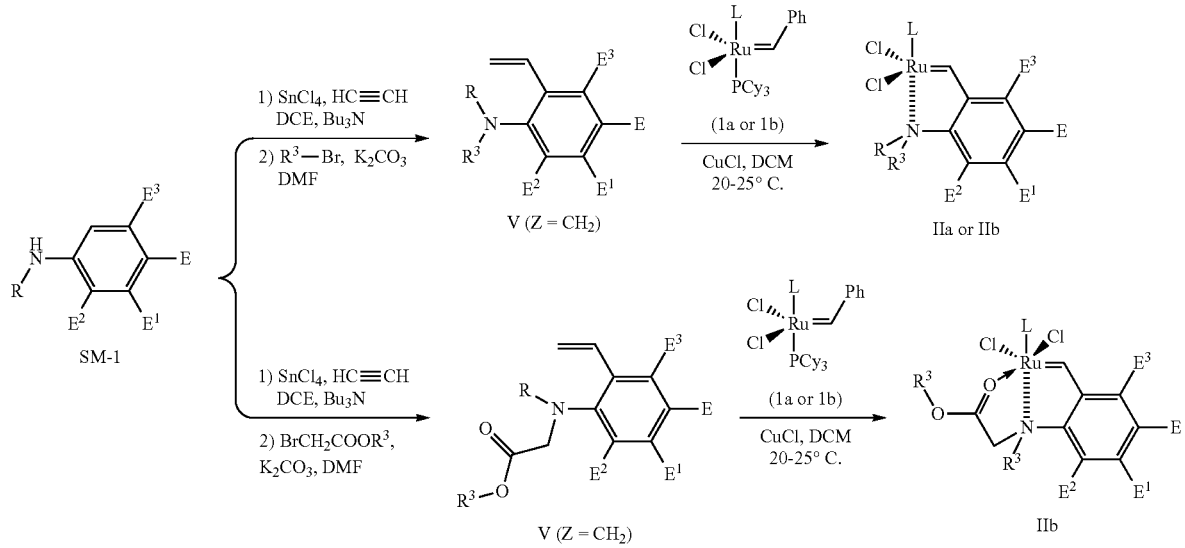

1a: L = $PCy_3$, Cy = Cyclohexyl  1b: L = $H_2IMes$ (1,3-dimesityl-4,5-dihydroimidazol-2-ylidene)

In Scheme 3, it is a common step to prepare diversity of substituted 2-aminostyrene ligands (V) by Wittig reaction with SM-2 first, followed by reaction with a Ru complex reagent (1a or 1b) to form the desired Ru complex catalyst Ia or Ib as follows:

Scheme 3:

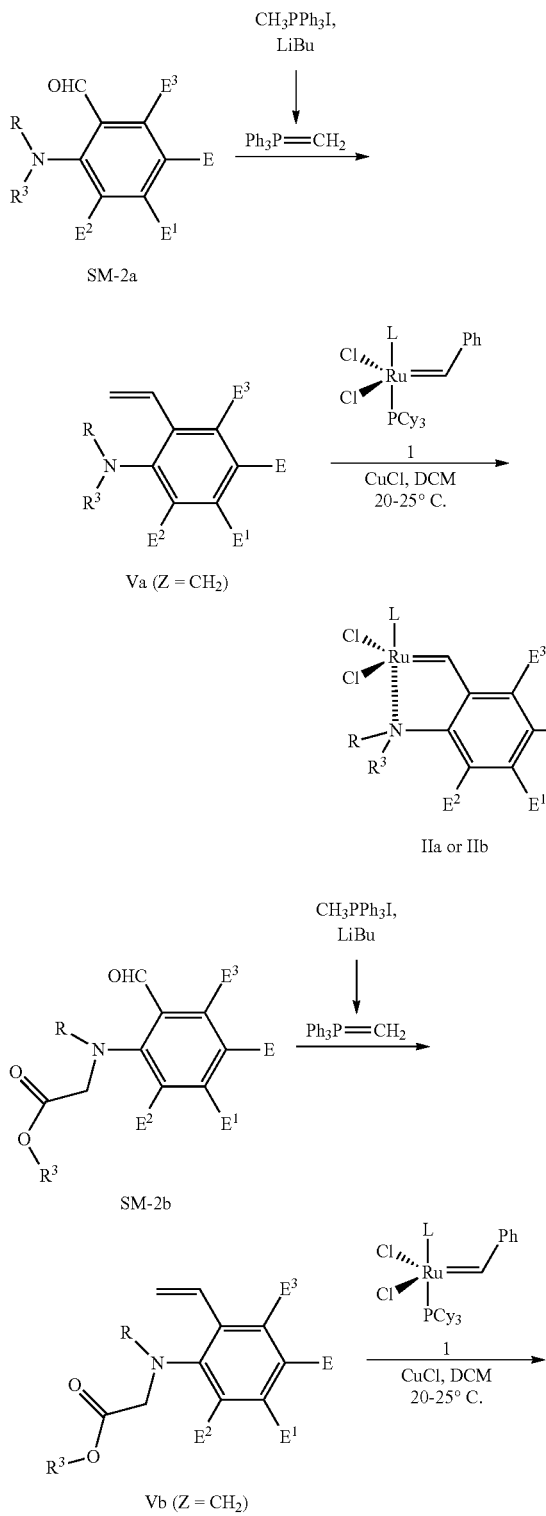

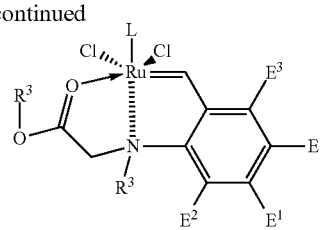

IIb

1a: L = PCy$_3$, Cy = Cyclohexyl
1b: L = H$_2$IMes (1,3-dimesityl-4,5-dihydroimidazol-2-ylidene)

In Scheme 4, SM-3 reacts with NaOEt in anhydrous EtOH to form carbene in a flask filled with inert gas, followed by reacting with reagent RuCl$_2$P(Ph$_3$)$_3$ and a ligand compound IIIa or IIIb (Z=CH$_2$) to form complex Va or Vb. The complex Va or Vb is reacted with IIa or IId effectively to obtain the Ru complex IIa or IIb, respectively.

Scheme 4:

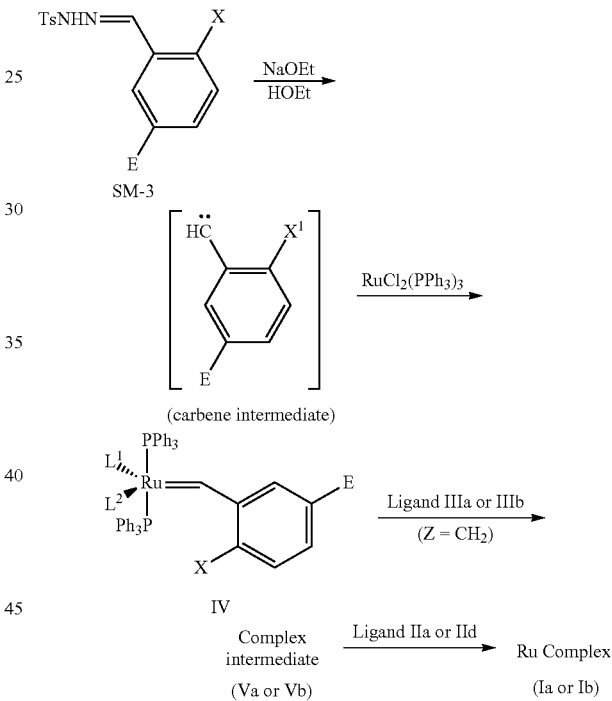

Significant Electronic Effect of Various Substituted Benzylidene Ligands on the Activity and Stability of Ru Complexes:

To study the electronic and steric effects of multi-substituted benzylidene ligands on the activity and selectivity of Ru complexes, based on different described synthetic methods and procedures in Schemes 2-4, different kinds of the complex ligands IIIa-IIIb (e.g., 3a-3bf, 5a-5j, 7a-7r, 9a-9j) have been prepared and reacted with the Ru complex 1a or 1b to produce different kinds of new Ru complexes Ia-Ib (e.g., 4a-4bf, 6a-6j, 8a-8r, 10a-10j, 11a-11r) in the present invention. Moreover, during preparation and activity evaluation of various Ru complexes with various substituted benzylidene ligands in the following Schemes 5-9, the significant electron-withdrawing and/or electron-donating effect of different substituted benzylidene ligands on the selective activity of Ru complexes for ROMP and RCM reactions has been observed as shown in Equations 1-9 and Tables 1-6, and some novel Ru catalysts have been prepared much more active and selective than prior reported Ru catalysts for different kinds of ROMP and RCM reactions.

Currently, the present invention provides the following significant achievements:

1. Two classes of novel carbene ligands and ruthenium complexes have been designed and prepared; and the electronic and steric effect of different substituted ligands on the catalytic activity and stability of various Ru complexes have been investigated. It is determined that some of novel Ru catalysts in the present invention have much better catalytic selectivity and variable physical diversity than Grubbs and Hoveyda catalysts in the ROMP and RCM reactions.

2. The experimental results show that some of novel Ru catalysts in the present invention have high activity and selectivity for different olefin ROMP and RCM reactions, so the invention provides a useful synthetic method of carrying out olefin metathesis reactions effectively in preparation of polymer materials and pharmaceutical intermediates.

3. The present invention provides several developed methods for preparation of carbene ligands and Ru catalysts at lower cost, and it also provides some efficient methods for preparation of various functional polymer materials with different chemical and physical properties.

4. The present invention provides several developed processes of conducting ROMP reaction with one or two more mixed of novel active Ru catalysts for preparation of the high-strength polymer materials and some functional polymers linked with small molecule pro-drugs and/or liquid crystal materials.

According to previously described synthetic methods, different new Ru complexes 4a-4bf have been prepared by the reaction listed in Scheme 5, and the corresponding metathesis activity of each Ru complex has been studied for RCM and ROMP reactions with different olefin substrates, respectively.

Scheme 5:

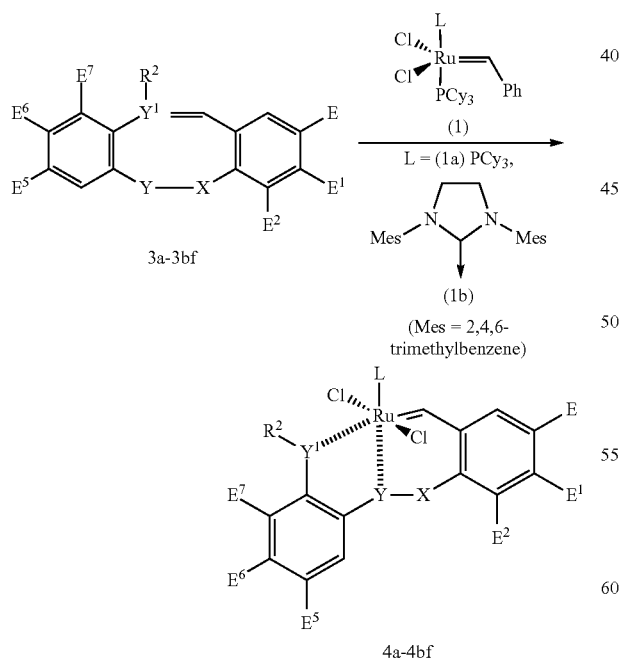

Some selected structure of prepared ruthenium complexes 4a-4bf (1a: Cy=cyclohexyl, and 1b: Mes=2,4,6-trimethylbenzene) is listed as follows:

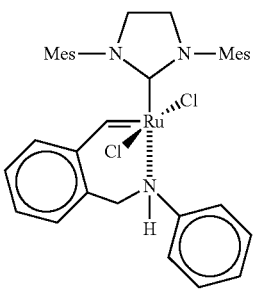

4a

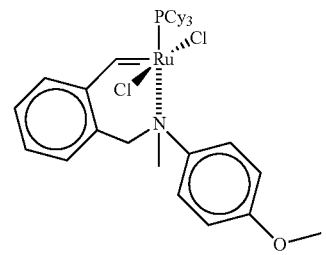

4b

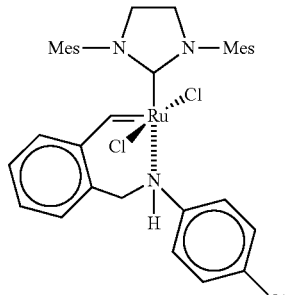

4c

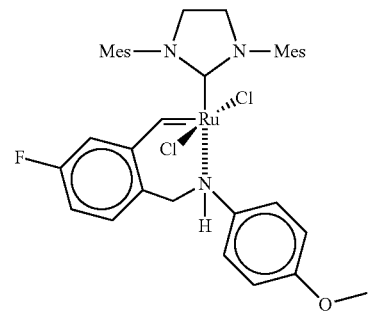

4d

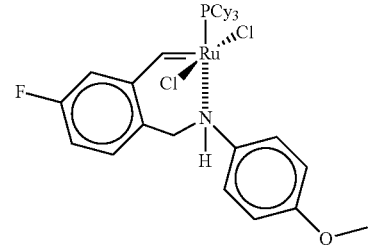

4e

4f
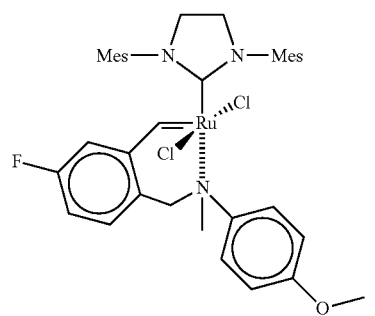
4g
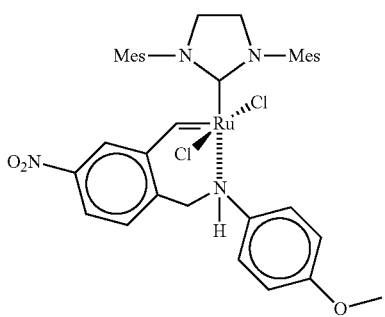
4h
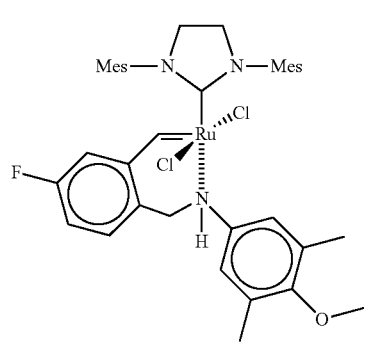
4j
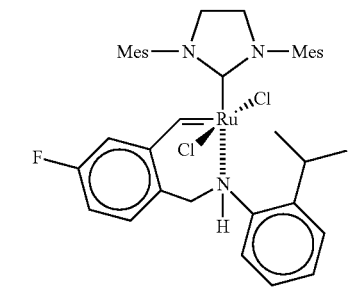
4k
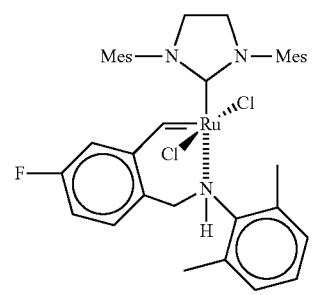
4m
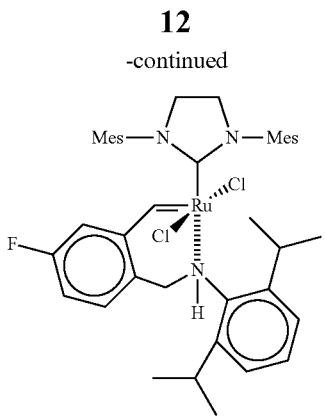
4n
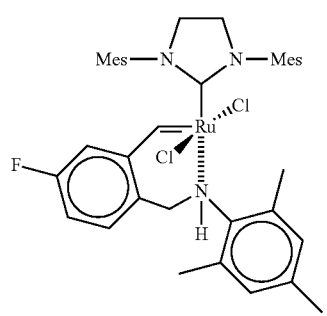
4p
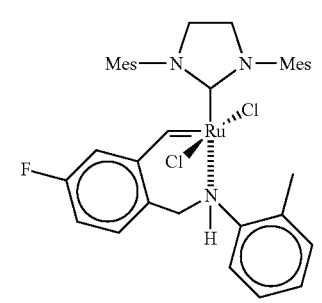
4q
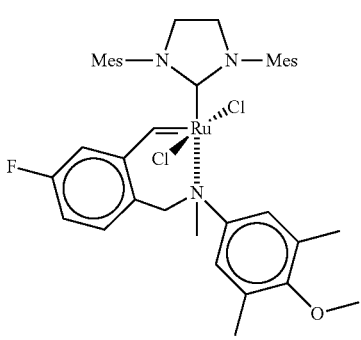
4r
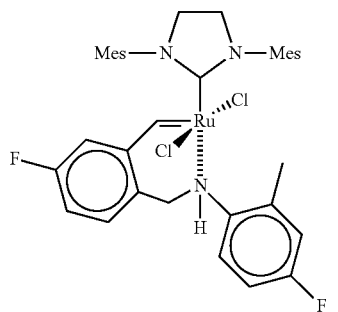

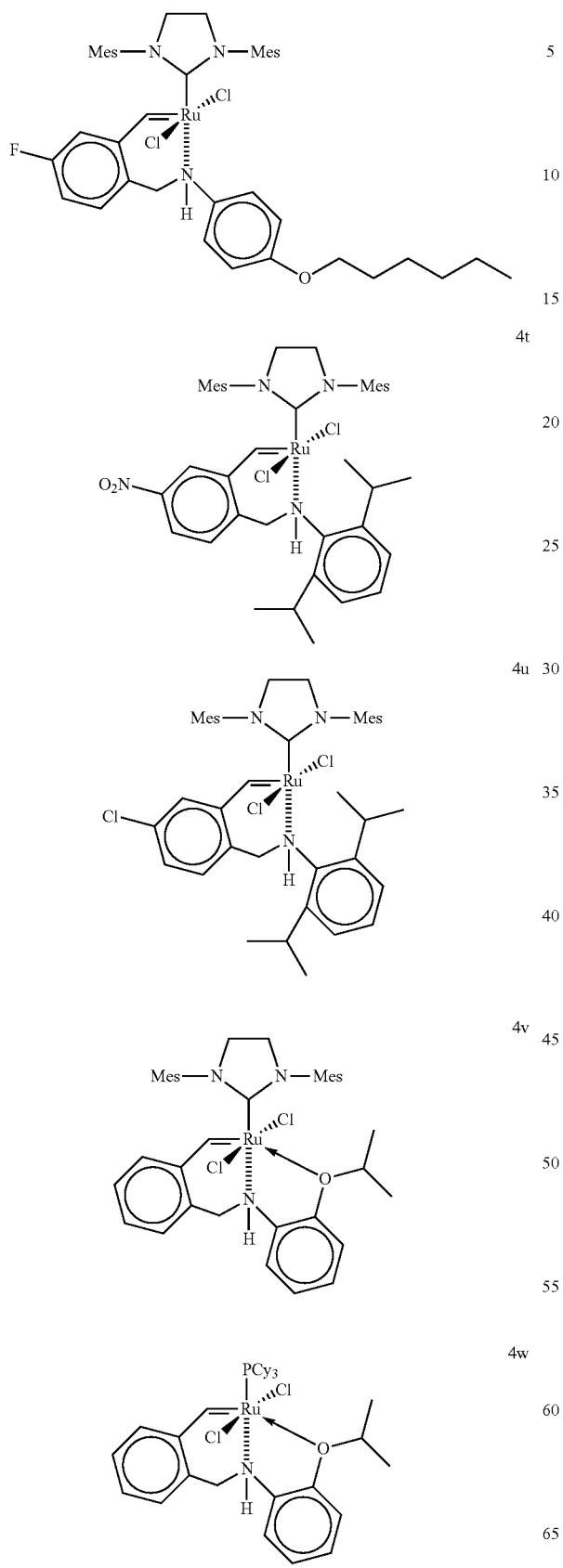
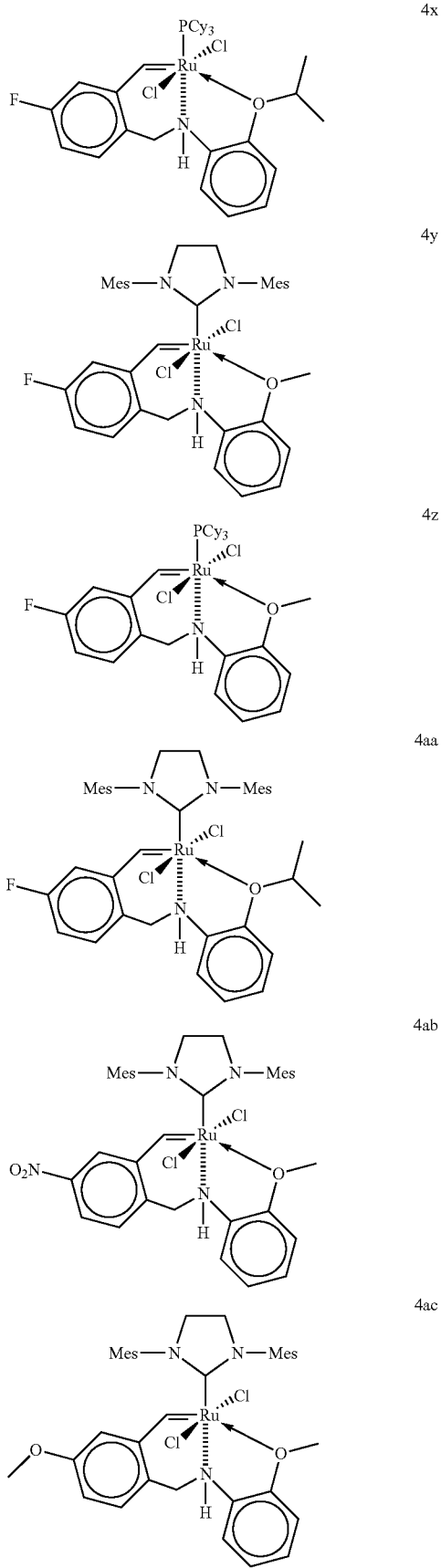

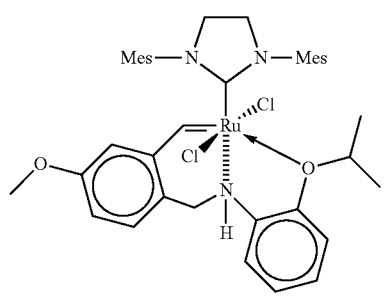
4ad
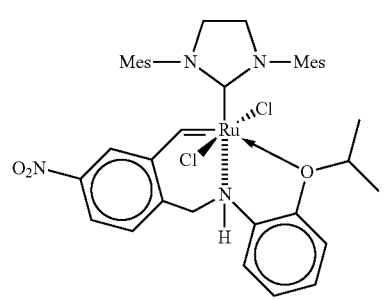
4ae
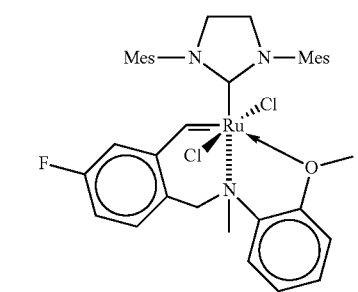
4af
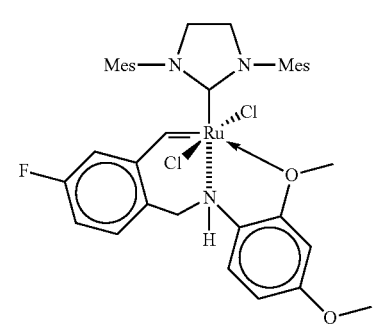
4ag
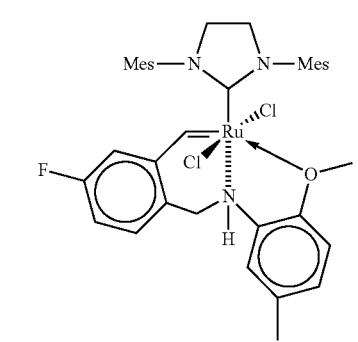
4ah
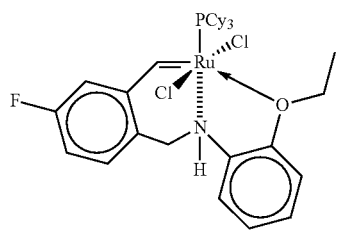
4aj
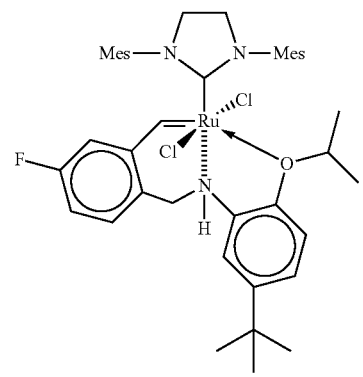
4ak
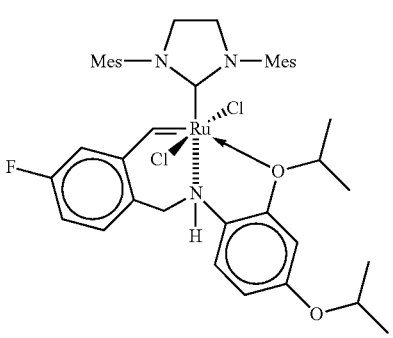
4am
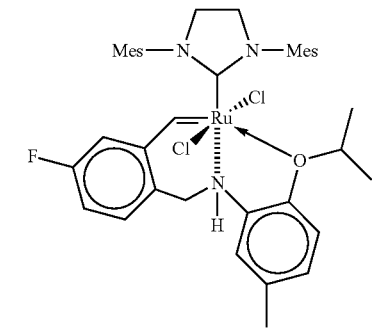
4an
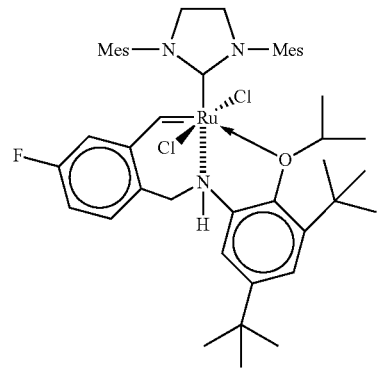
4ap

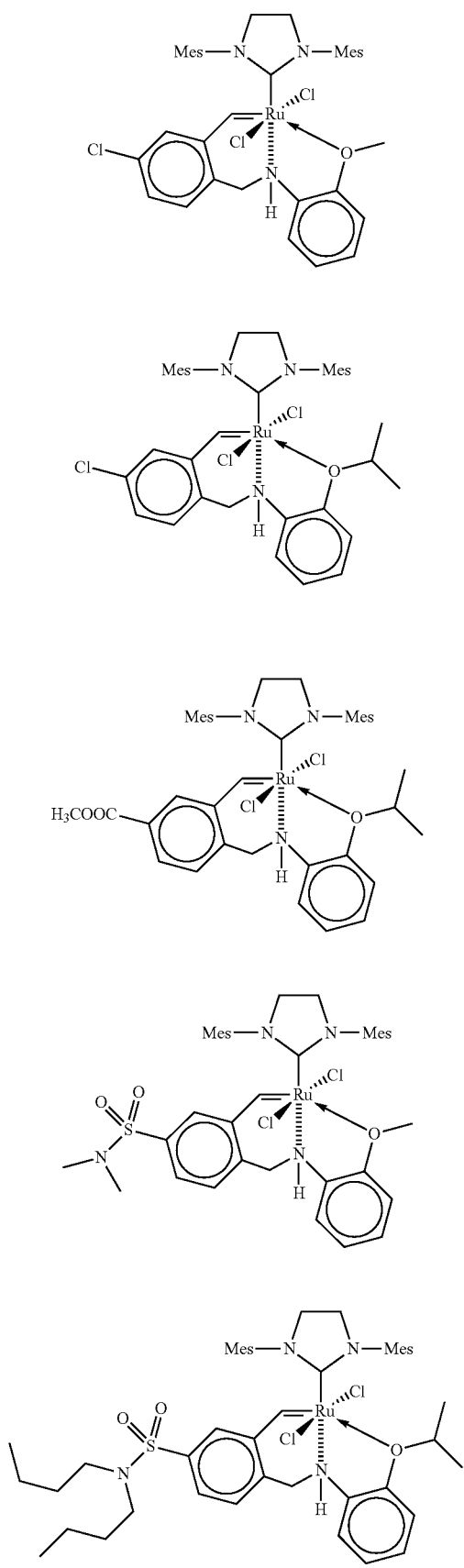
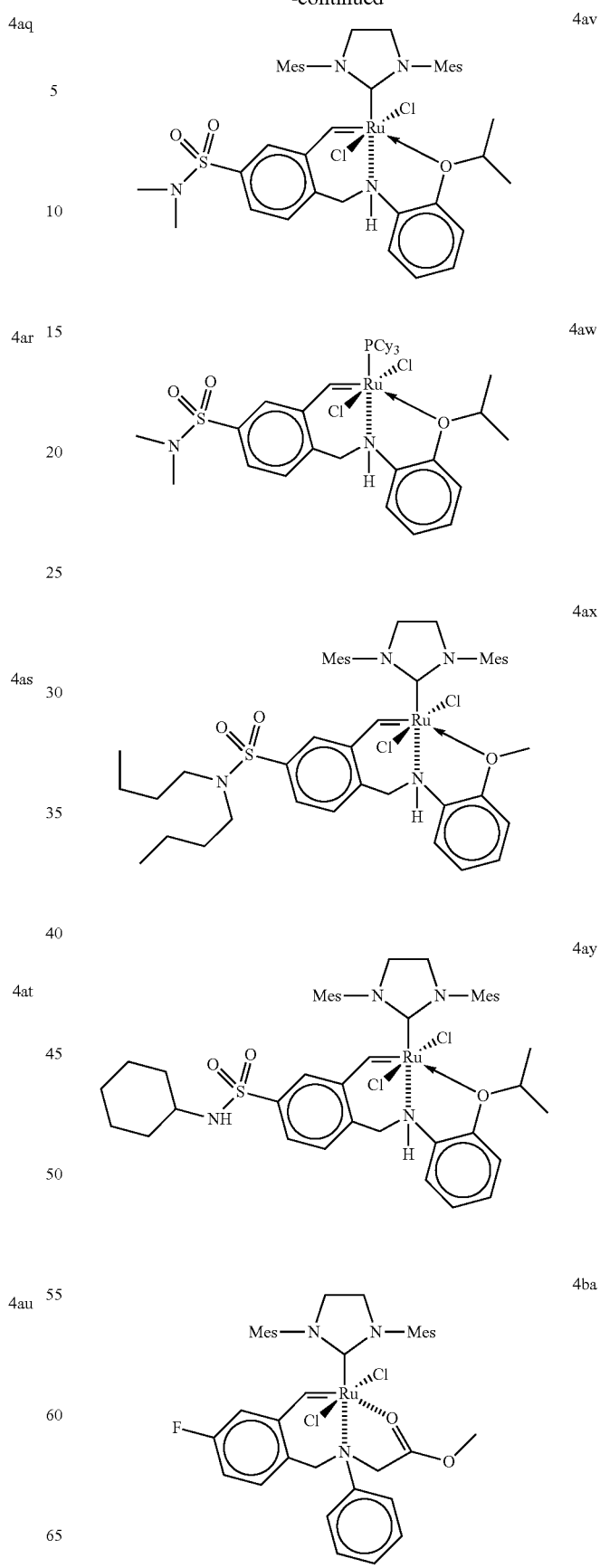

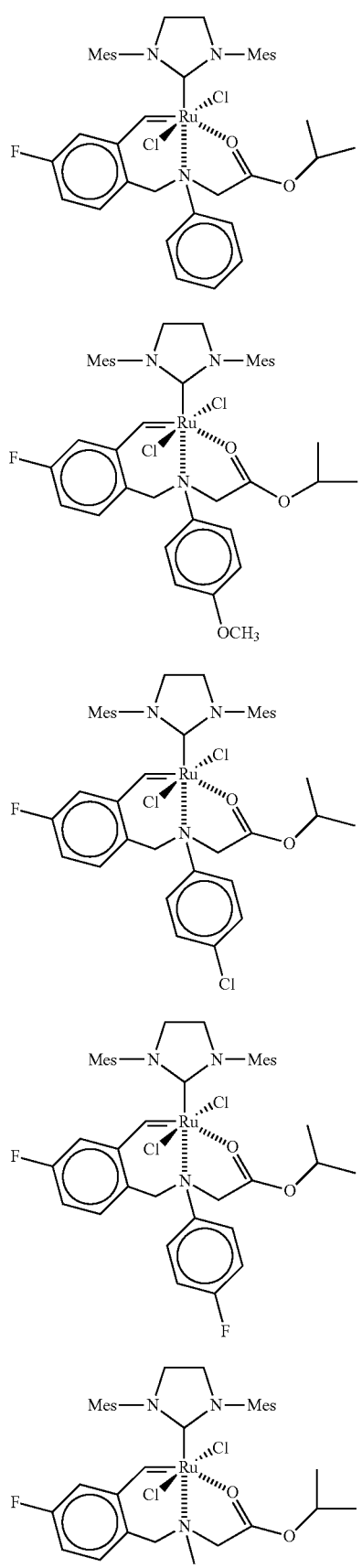

According to previously described synthetic methods, various new Ru complexes 6a-6j have been prepared by the reaction listed in Scheme 6, and the corresponding metathesis activity of each Ru complex has been studied for RCM and ROMP reactions with different olefin substrates, respectively.

Scheme 6:

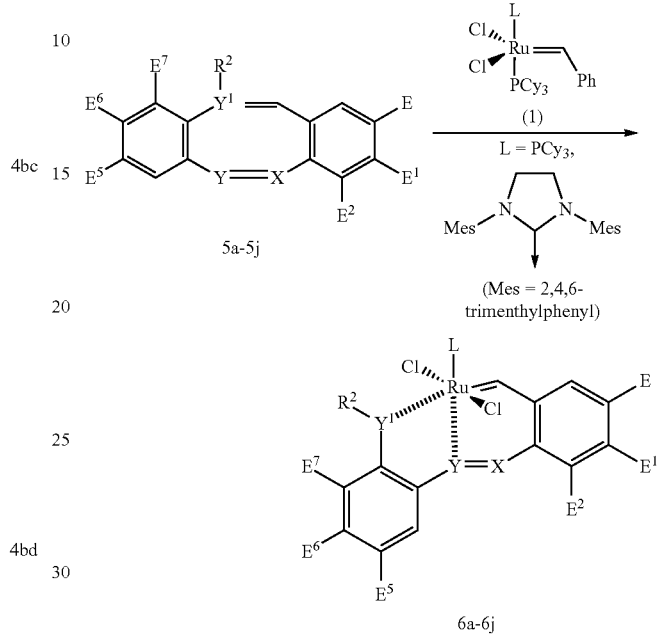

Some selected structure of prepared ruthenium complexes 6a-6j (1a: L=PCy$_3$, and Cy=cyclohexyl; 1b: Mes=2,4,6,-trimethylbenzene) is listed as follows:

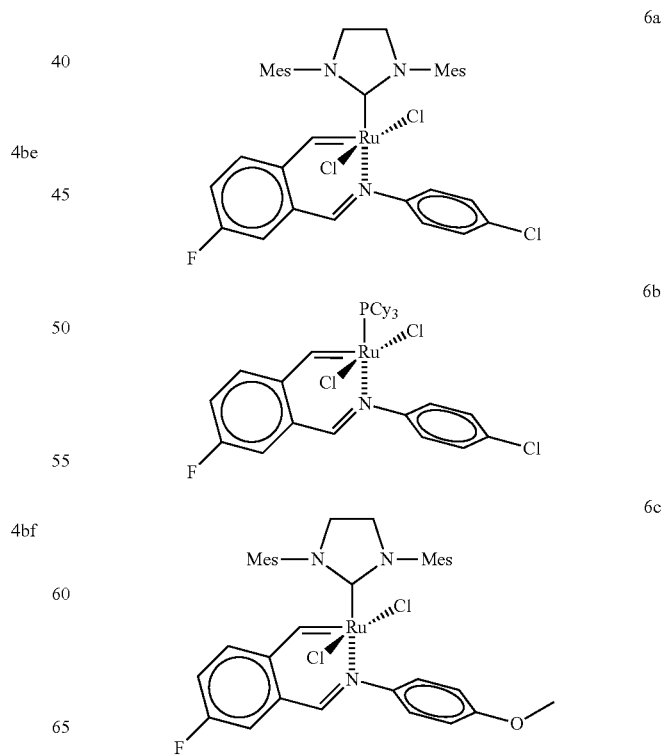

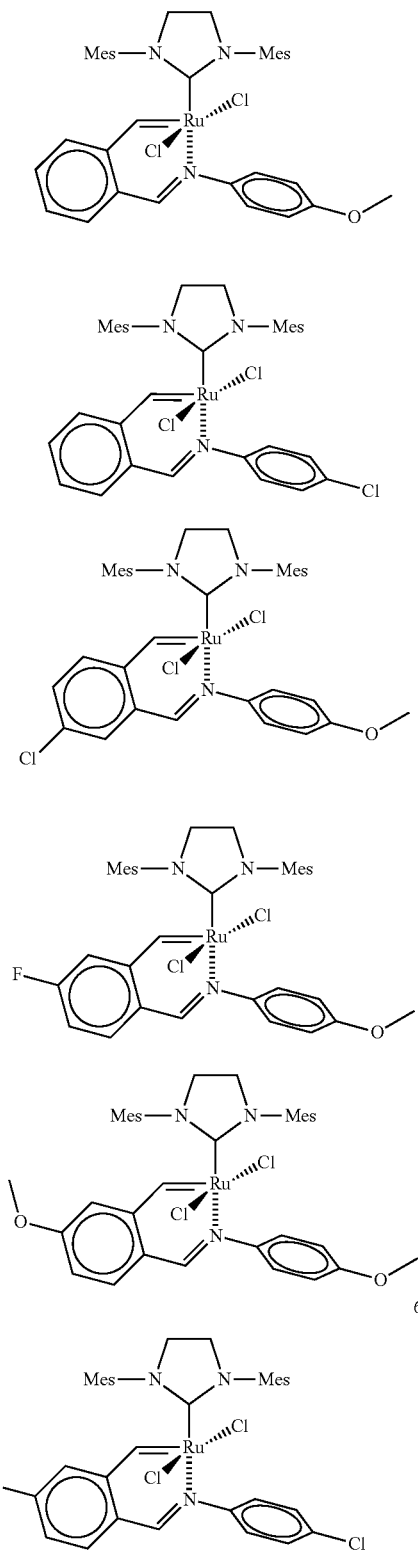

6d

6e

6f

6g

6h 6j (Unstable)

Scheme 7:

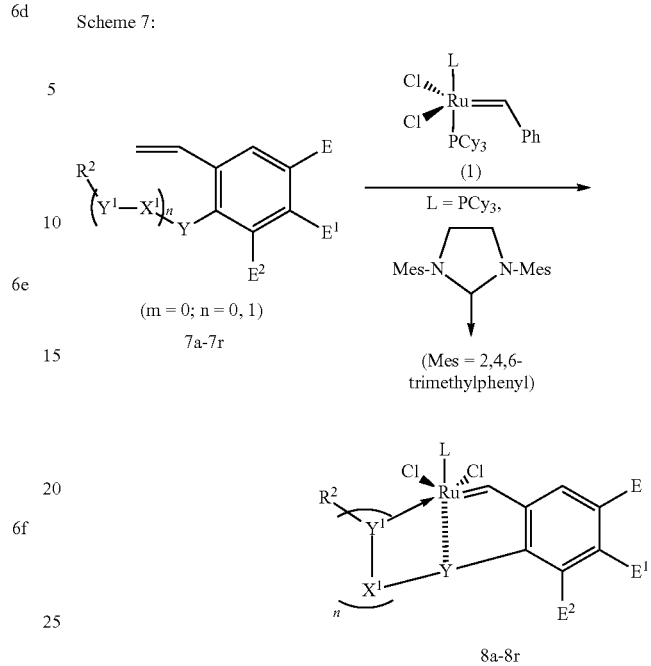

(m = 0; n = 0, 1)
7a-7r (Mes = 2,4,6-trimethylphenyl)

8a-8r

Some selected structure of prepared ruthenium complexes 8a-8r (1a: L=PCy$_3$, and Cy=cyclohexyl; 1b: Mes=2,4,6,-trimethylbenzene) is listed as follows:

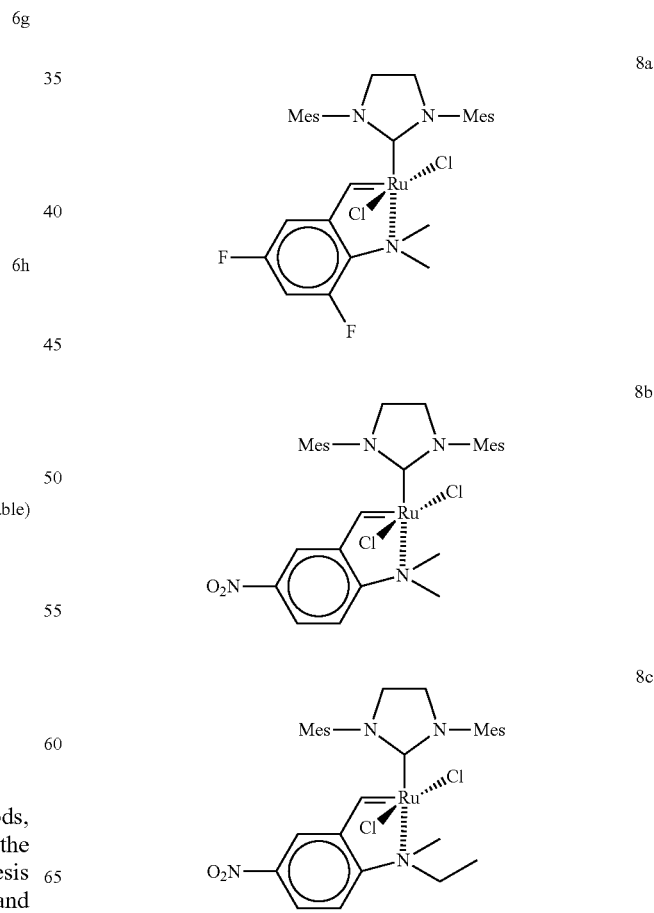

According to previously described synthetic methods, various new Ru complexes 8a-8r have been prepared by the reaction listed in Scheme 7, and the corresponding metathesis activity of each Ru complex has been studied for RCM and ROMP reactions with different olefin substrates, respectively.

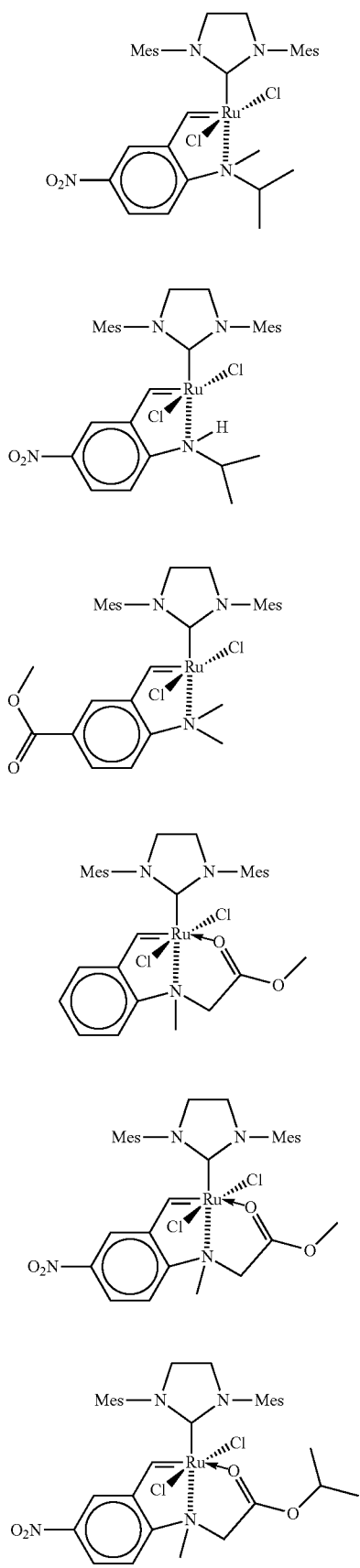
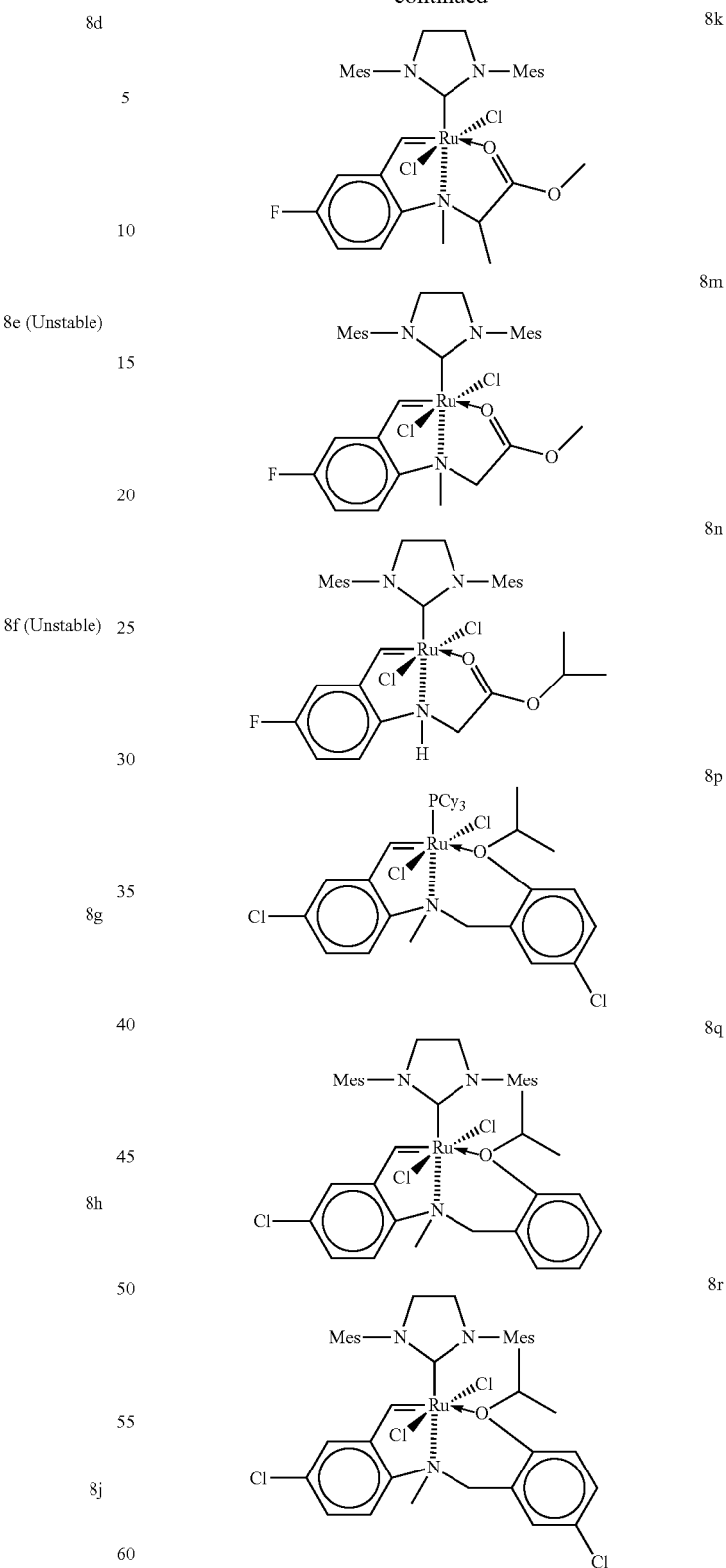
The structure of Ru catalyst 8m above is confirmed by single-crystal X-ray as shown in FIG. 1.
According to previously described synthetic methods, various new Ru complexes 10a-10j have been prepared by the reaction listed in Scheme 8, and the corresponding metathesis activity of each Ru complex has been studied for RCM and ROMP reactions with different olefin substrates, respectively.
Scheme 8:
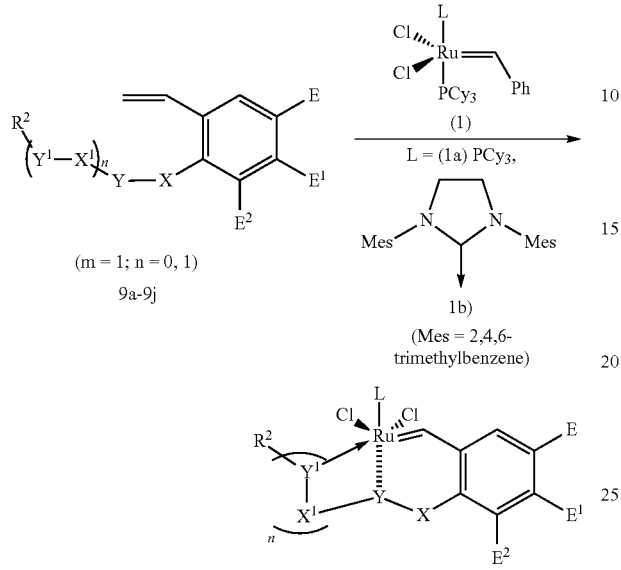
(m = 1; n = 0, 1)
9a-9j
L = (1a) PCy₃,
1b)
(Mes = 2,4,6-trimethylbenzene)
10a-10j
Some selected structure of prepared ruthenium complexes 10a-10j (1a: L=PCy₃, and Cy=cyclohexyl; 1b: Mes=2,4,6,-trimethylbenzene) is listed as follows:
10a (Unstable)
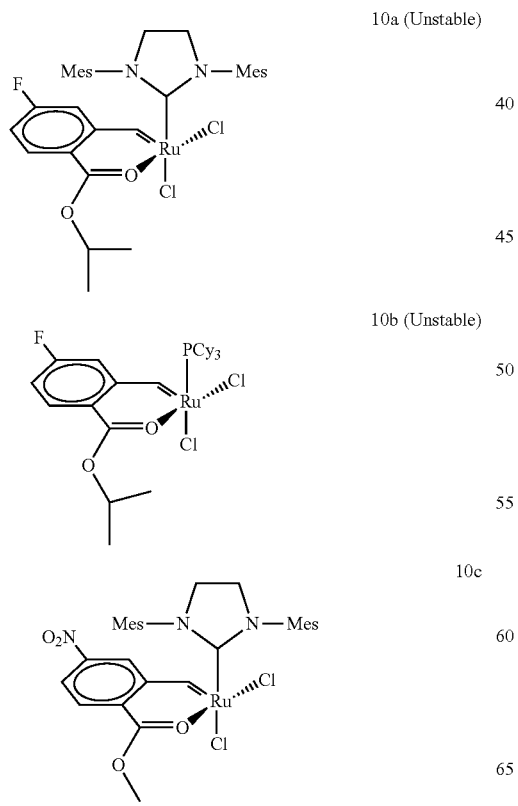
10b (Unstable)
10c
-continued
10d
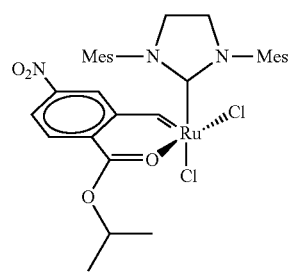
10e
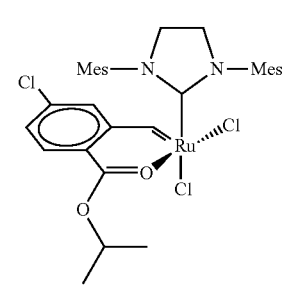
10f
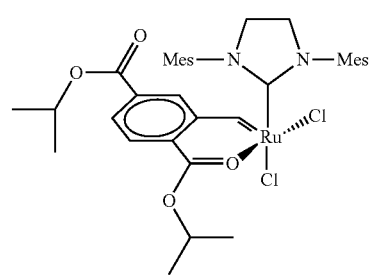
10g
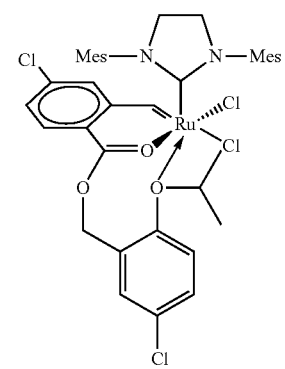
10h
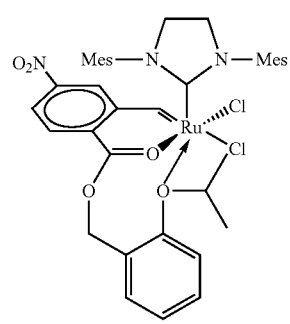

-continued

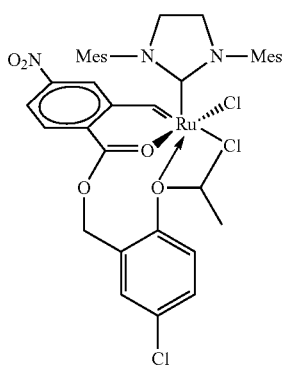

10j

According to previously described synthetic methods, various new Ru complexes 11a-11r have been prepared by the reaction listed in Scheme 9, and the corresponding metathesis activity of each Ru complex has been studied for RCM and ROMP reactions with different olefin substrates, respectively.

Scheme 9:

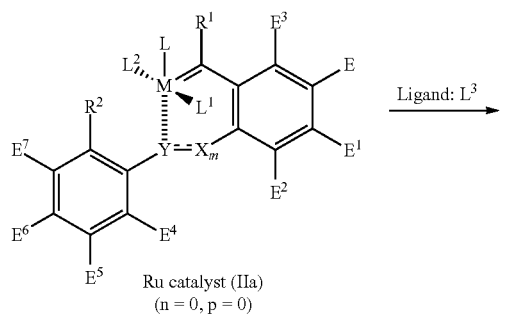

Ru catalyst (IIa)
(n = 0, p = 0)

Ligand: L³

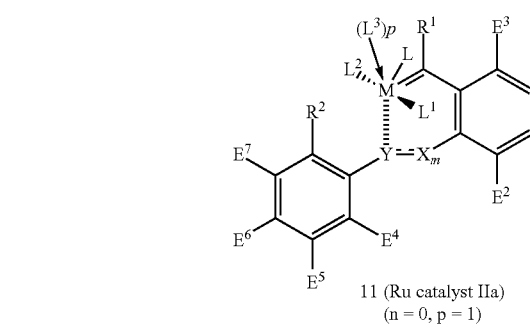

11 (Ru catalyst IIa)
(n = 0, p = 1)

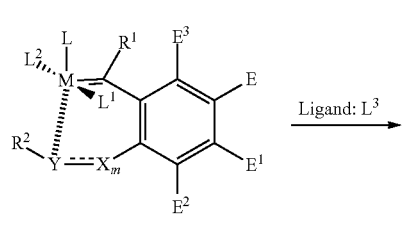

Ru catalyst (IIb)
(n = 0, p = 0)

Ligand: L³

-continued

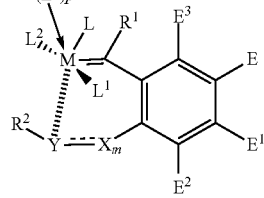

11 (Ru catalyst IIb)
(n = 0, p = 1)

Some selected structure of prepared ruthenium complexes 11a-11r (1a: L=PCy$_3$, and Cy=cyclohexyl; 1b: Mes=2,4,6,-trimethylbenzene) is listed as follows:

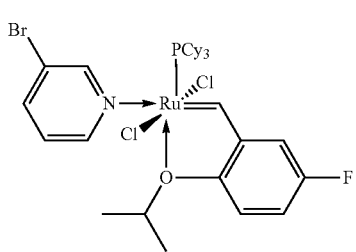

11a

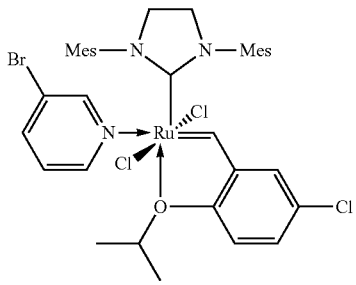

11b

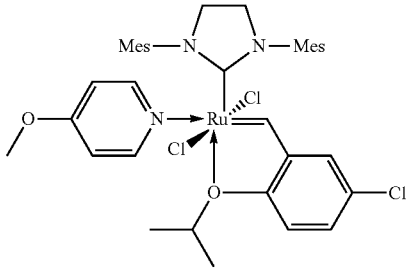

11c

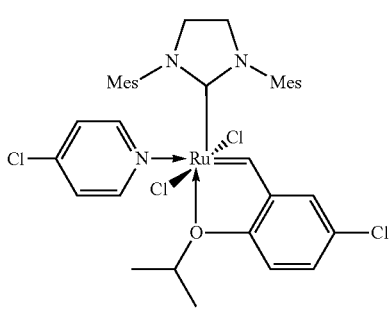

11d

11e 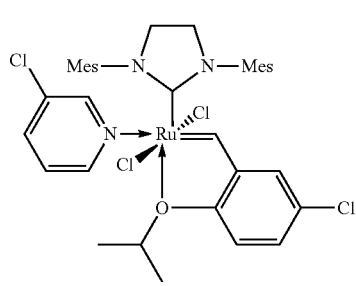
11j 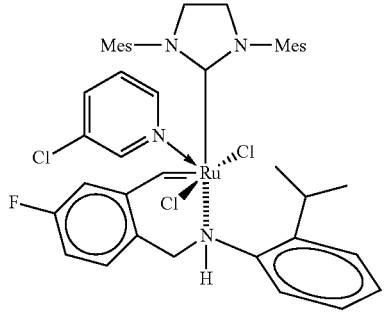
11f 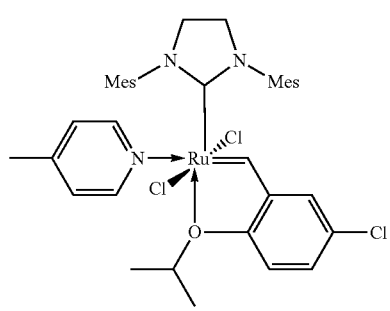
11k 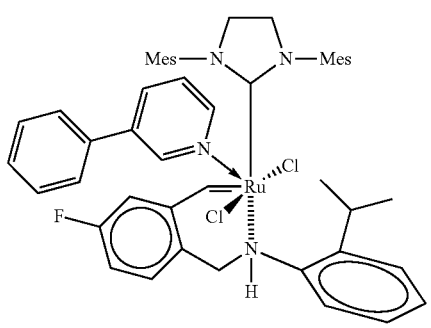
11g 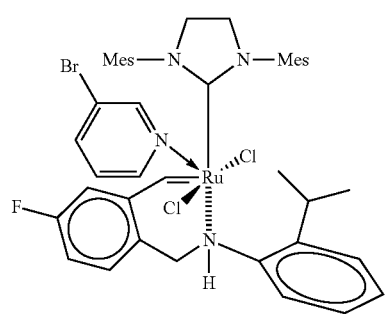
11m 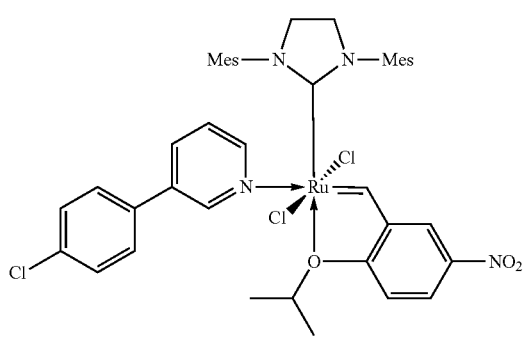
11h 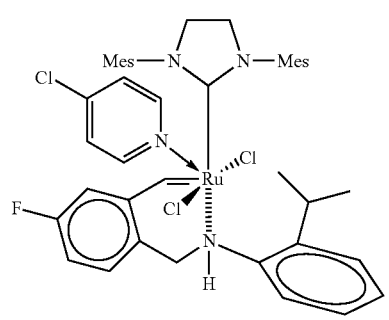
11n 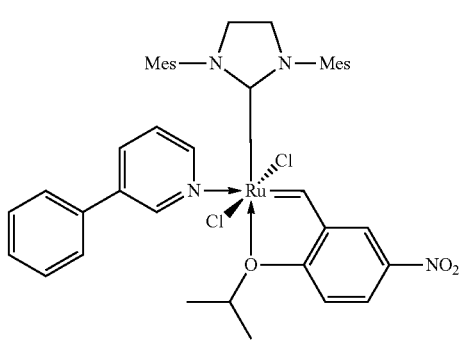

31
-continued

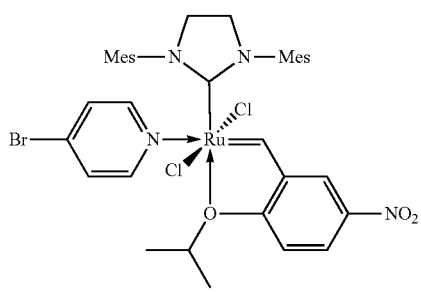

11p

11q

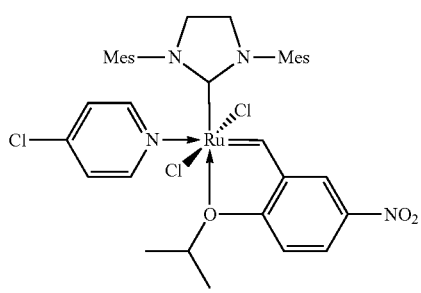

32
-continued

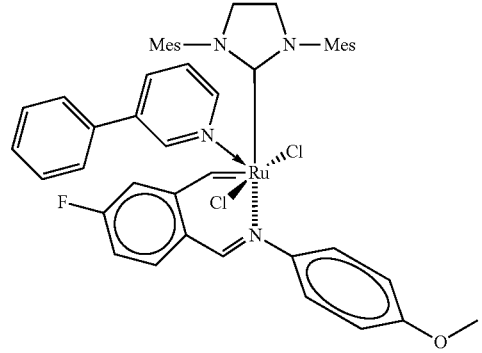

11r

Two Alternative Production Procedures for Preparation of Some Highly Active Metathesis Catalysts:

In order to prepare different kinds of Ru catalyst at lower cost, based on some references (Zhan et al., US20070043180A1 and WO2007003135A1) and new process development as described in Schemes 10 and 11, there is the following alternative procedure developed in Scheme 9 for scale-up production of different Ru catalysts in the present invention.

Scheme 10: A convenient route for preparation of some Ru complexes

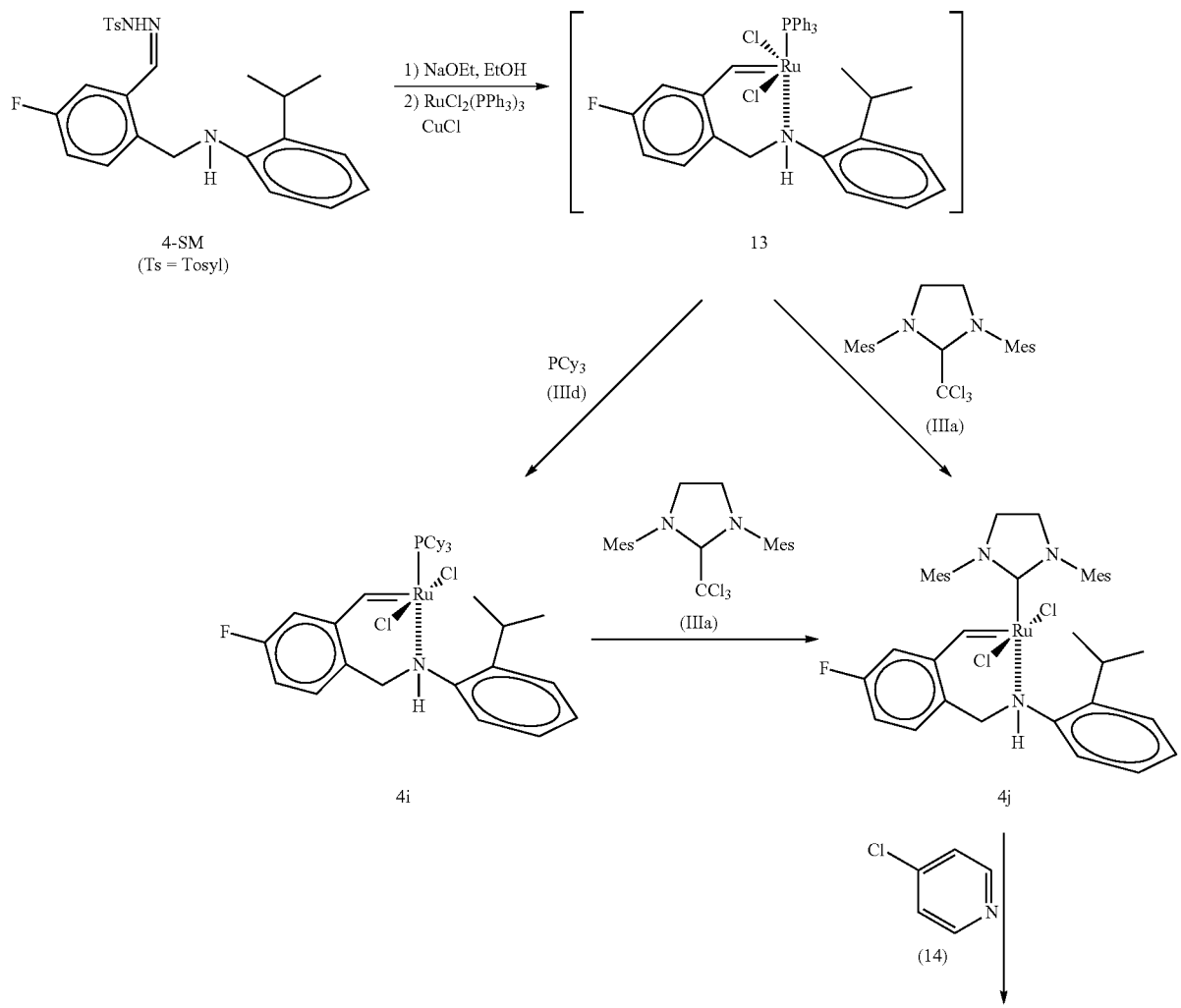

-continued

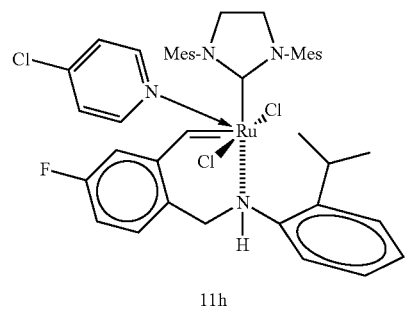

11h

In Scheme 10, the starting material 4-SM was reacted with sodium ethoxide to produce carbene intermediate 12 first, followed by reacting with RuCl$_2$(PPh$_3$)$_3$ directly to form Ru complex intermediate 13. The triphenylphosphine ligand (PPh$_3$) of Ru intermediate 13 was replaced by another ligand PCy$_3$ (IIId) to form a new Ru complex 4i. The phosphine ligand of Ru intermediate 13 or 4i was further replaced by an NHC ligand (H$_2$IMes, IIIa) to form another Ru complex 4j. The Ru complex 4j could directly react with another ligand 4-chloro pyridine (14) to make the Ru to complex 11h.

and the kinetic results of different conducted RCM and ROMP reactions for each new catalyst are listed in Tables 1, 2, 3, 4 and 5, respectively. Other eight prior known Ru catalysts 1a-1b and 2a-2f listed in Scheme 1 are also selected for evaluation of metathesis activity study with various substrates 15, 17, 19, 21, 23, 25, 27, 29 and 31 in comparison to all new Ru catalysts in the present invention.

The evaluation of catalytic activity for RCM in Equation 1 with different catalysts 4a-4bf, 6a-6j, 8a-8r, 10a-10j, and 11a-11r has been done under the same reaction condition, and Scheme 11: A convenient route for preparation of some Ru complexes

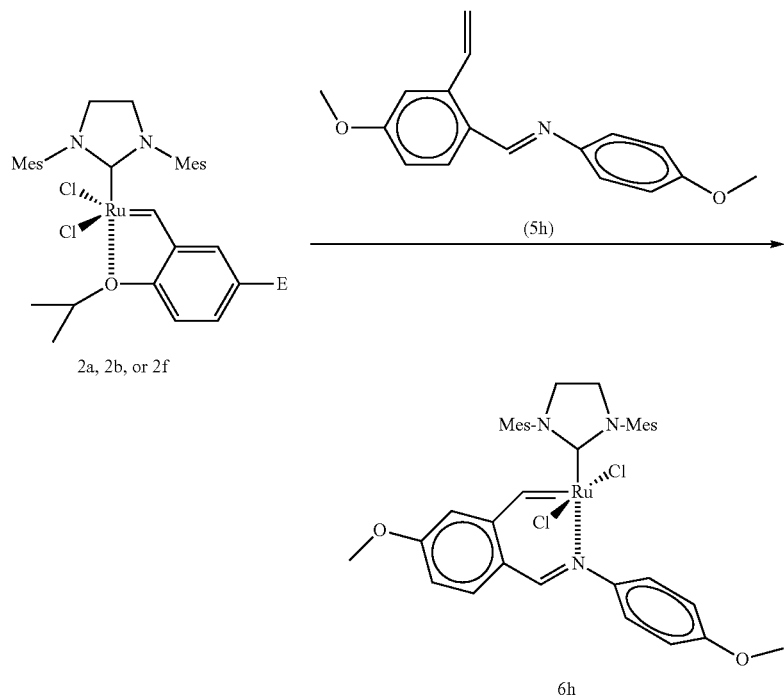

2a, 2b, or 2f

6h

In Scheme 11, the Ru complex (e.g., Hoveyda catalyst 2a; Zhan Catalyst 2b; or Grela catalyst 2f) could directly react with a ligand 5h to form the desired Ru complex 6h in good yield.

So far, to study the relative activity and catalytic selectivity of above prepared catalysts 4a-4bf, 6a-6j, 8a-8r, 10a-10j, and 11a-11r, two olefin substrates 15 and 17 in Equations 1 and 2 were designed for evaluation of RCM reactions, a kind of diene substrates 19 was designed for evaluation of Cross Metathesis (CM) reaction in Equation 3, and different kinds of cyclic olefin substrates 21, 23, 25, 27, 29 and 31 were designed for evaluation of ROMP reactions in Equations 4-9, the valuable experimental data for different Ru catalysts are selected and listed in Tables 1-1 to 1-4, respectively.

Equation 1:

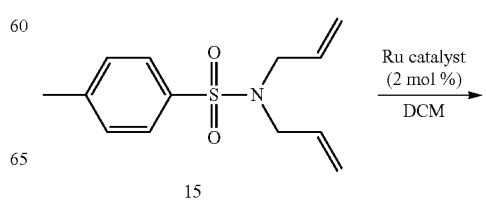

15

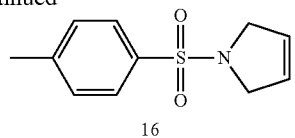

16

TABLE 1-1

Activity Results of Some Selected Complexes 4a-4bf for Substrate 15

| Entry | Catalyst | Conversion (% by HPLC) | | | |
|---|---|---|---|---|---|
| | | 10 min | 30 min | 1.5 hr | 3.0 hr |
| 1 | 4a | 40 | 81 | 98 | |
| 2 | 4b | 52 | 85 | 98 | |
| 3 | 4f | 84 | 94 | 96 | 100 |
| 4 | 4g | 94 | 100 | | |
| 5 | 4u | 96 | 100 | | |
| 6 | 4v | 41 | 71 | 93 | 100 |
| 7 | 4y | 43 | 66 | 87 | 94 |
| 8 | 4aa | 21 | 59 | 82 | 92 |
| 9 | 4ab | 94 | 100 | | |
| 10 | 4ac | 70 | 90 | 100 | |
| 11 | 4af | 93 | 97 | | |
| 12 | 4aj | 95 | 99 | | |
| 13 | 4ap | 71 | 82 | 93 | 98 |
| 14 | 4at | 24 | 48 | 73 | 100 |
| 15 | 4ba | 62 | 73 | 79 | 85 |
| 16 | 4bb | 100 | | | |
| 17 | 4bc | 94 | 100 | | |
| 18 | 4bd | 68 | 81 | 84 | 89 |
| 19 | 4be | 100 | | | |

Among Ru complexes 4a-4bf, only some of new complexes (such as 4f, 4g, 4u, 4ab, 4aj, 4bb and 4be) show high catalytic activity, the rest of them not listed in Table 1-1 have lower or very poor activities for RCM reaction. Based on the determined results in Table 1-1, the activity of Ru complexes 4a-4bf for RCM is significantly affected by the electronic and steric effect of different substituents incorporated in various new ligands 3a-3bf. However, some of complexes 4a-4bf non-active for RCM can be used effectively in the following ROMP (Equations 3-9) with high activity and selectivity.

TABLE 1-2

Activity Results of Some Selected Complexes 6a-6j for Substrate 15

| Entry | Catalyst | Conversion (% by HPLC) | | | |
|---|---|---|---|---|---|
| | | 10 min | 30 min | 1.5 hr | 3.0 hr |
| 1 | 6e | 0 | 0 | 0 | 0 |
| 2 | 6h | 95 | 100 | | |
| 3 | 6j | 45 | 70 | 89 | 95 |
| 4 | 2e | 0 | 0 | 0 | 0 |

Among complexes 6a-6j, only a Ru complexes 6h shows high catalytic activity and much better than the known catalyst 2e, the rest of them not listed in Table 1-2 have worse or very poor activities. Based on the determined results in Table 1-2, the activity of Ru complexes 6a-6j for RCM is significantly affected by the electronic and steric effect of different substituents incorporated in various new ligands 5a-5j. However, some of complexes 6a-6j non-active for RCM can be used effectively in the following ROMP (Equations 3-9) with high activity and selectivity.

TABLE 1-3

Activity Results of Some Selected Complexes 8a-8r for Substrate 15

| Entry | Catalyst | Conversion (% by HPLC) | | | |
|---|---|---|---|---|---|
| | | 10 min | 30 min | 1.5 hr | 3.0 hr |
| 1 | 8b | 73 | 79 | 98 | |
| 2 | 8g | 0 | 0 | 0 | 0 |
| 3 | 8h | 96 | 98 | 99 | |
| 4 | 8q | 53 | 76 | 88 | 99 |
| 5 | 8r | 79 | 93 | 100 | |
| 6 | 2c | 47 | 69 | 82 | 92 |

Among complexes 8a-8r, only a few complexes (such as 8b, 8h and 8r) show good catalytic activity and much better than the known catalyst 2c, the rest of them not listed in Table 1-3 have worse or very poor activities. Based on the determined results in Table 1-3, the activity of Ru complexes 8a-8r for RCM is significantly affected by the electronic and steric effect of different substituents incorporated in various new ligands 7a-7r. However, some of non-active complexes 8a-8r for RCM can be used effectively in the following ROMP (Equations 3-9) with high activity and selectivity.

TABLE 1-4

Activity Results of Some Selected Complexes 10a-10j for Substrate 15

| Entry | Catalyst | Conversion (% by HPLC) | | | |
|---|---|---|---|---|---|
| | | 10 min | 30 min | 1.5 hr | 3.0 hr |
| 1 | 10c | 90 | 99 | | |
| 2 | 10d | 96 | 100 | | |
| 3 | 10e | 91 | 96 | 100 | |
| 4 | 10g | 84 | 99 | | |
| 5 | 10j | 86 | 92 | 99 | |
| 6 | 2d | 62 | 78 | 90 | 98 |

Among complexes 10a-10j, several complexes (such as 10c, 10d, 10e and 10g) show good or high catalytic activity and much better than the known catalyst 2d, the rest of them not listed in Table 1-4 have worse or very poor activities. Based on the determined results in Table 1-4, the activity of Ru complexes 10a-10j for RCM is significantly affected by the electronic and steric effect of different substituents incorporated in various new ligands 9a-9j. However, some of non-active complexes 10a-10j for RCM can be used effectively in the following ROMP (Equations 3-9) with high activity and selectivity.

TABLE 1-5

Activity Results of Some Selected Complexes 11a-11r for Substrate 15

| Entry | Catalyst | Conversion (% by HPLC) | | | |
|---|---|---|---|---|---|
| | | 10 min | 30 min | 1.5 hr | 3.0 hr |
| 1 | 11b | 38 | 57 | 60 | 61 |
| 2 | 11e | 44 | 57 | 65 | 68 |
| 3 | 11p | 39 | 43 | 45 | 45 |
| 4 | 11q | 32 | 34 | 38 | 40 |

Among complexes 11a-11r, only a few complexes (such as 11c, 11e and 11p) show lower catalytic activity, the rest of them not listed in Table 1-5 have worse or very poor activities. Based on the determined results in Table 1-5, the activity of Ru complexes 11a-11r for RCM is significantly affected by the electronic effect of different substituented pyridine ligands. However, some of complexes 11a-11r non-active for RCM can be used effectively in the following ROMP (Equations 3-9) with high activity and selectivity.

In order to find some new catalysts with better activity and selectivity, it is designed to carry out a RCM reaction with a phenyl-substituted diene substrate 17 as shown in Equation 2 instead of unsubstituted diene substrate 15 for further evaluation of some active catalysts selected from the catalysts 4a-4bf, 6a-6j, 8a-8r, 10a-10j, and 11a-11r according to activity results in Tables 1-1 to 1-5. The experimental results of RCM activity for substrate 17 are listed in Tables 2.

Equation 2:

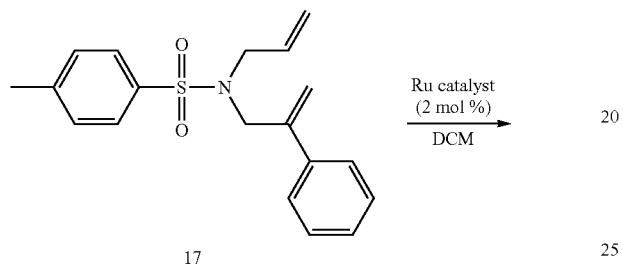

17

18

Equation 3:

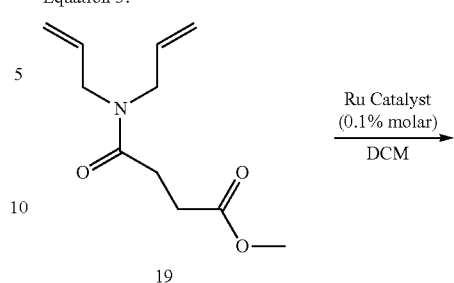

19

20

After screening with most of new Ru catalysts, it is found that some catalysts such as 8g and 8m could selectively catalyze the ROMP reaction effectively.

Equation 4:

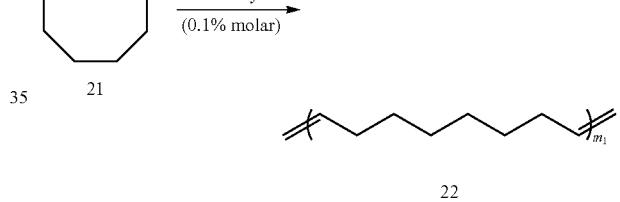

21

22

After screening with most of new Ru catalysts, it is found that some catalysts such as 4d and 8j could catalyze the ROMP reaction effectively.

Equation 5:

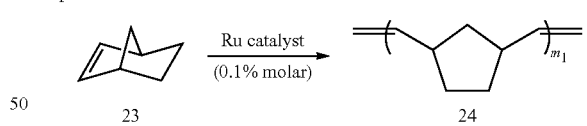

23

24

The ROMP results show that the catalysts 4b, 4f, 4v, 4y, 4aa, 8b and 8h of the present invention have better activity and selectivity for norbornene (23) polymerization. Catalytic polymerization was completed in 10-60 min, and the polymer product (24) has better tensile-strength when it is prepared as film.

Equation 6:

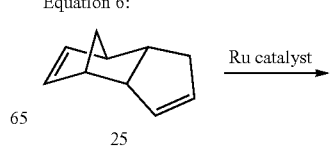

25

TABLE 2

Activity Results of Some Selected Ru Complexes for Substrate 17

| Entry | Catalyst | Conversion (% by HPLC) | | | |
| --- | --- | --- | --- | --- | --- |
| | | 10 min | 30 min | 1.5 hr | 3.0 hr |
| 1 | 4f | 67 | 86 | 94 | 99 |
| 2 | 4g | 61 | 78 | 86 | 98 |
| 5 | 4ab | 63 | 85 | 96 | 99 |
| 6 | 4ad | 51 | 68 | 79 | 95 |
| 7 | 4af | 72 | 86 | 92 | 99 |
| 8 | 4be | 49 | 73 | 86 | 91 |
| 9 | 6h | 70 | 88 | 90 | 96 |
| 10 | 8h | 75 | 88 | 96 | 99 |
| 11 | 10a | 42 | 65 | 81 | 98 |
| 12 | 10c | 71 | 82 | 85 | 92 |
| 13 | 10d | 82 | 94 | 95 | 100 |
| 14 | 10f | 35 | 63 | 83 | 99 |
| 15 | 10g | 46 | 69 | 84 | 100 |

To develop more effective ROMP catalysts and prepare better quality of new functional polymers, and also better to measure the difference of various active Ru catalysts, the evaluation of catalytic activity for different ROMP reactions in Equations 3-9 with different catalysts 4a-4bf, 6a-6j, 8a-8r, 10a-10j, and 11a-11r has been done under the same reaction condition, and some valuable results for different Ru catalysts are selected or listed in Tables 3 to 6, respectively. Based on the broad test, it is useful to find some active and selective catalysts for ROMP and RCM reactions, respectively.

-continued

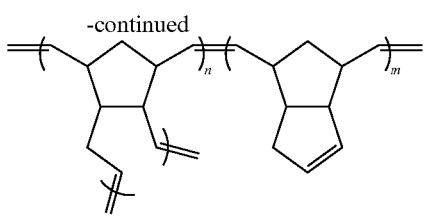

26

The ROMP results show that the catalysts 4b, 4f, 4v, 4y, 4aa, 4ag, 4ar, 4au, 8a, 8b, 8c, 8h, 8m and 8q of the present invention have better activity and selectivity for DCPD (25) polymerization. The ROMP polymerization was completed in 5-60 min for different Ru catalysts. The reaction temperature is preferred to be 40-60° C. By using one or two more mixed catalysts, it is surprised to obtain the high strength and high stiffness polymer PDCPD.

The property tests of various PDCPD (26) samples in the present invention show that several PDCPD products have more better tensile strength (55-62 Mpa) and flexural strength (78-83 Mpa) than those of commercial PDCPD products such as "Pentam, Metton, and Prometa" (tensile strength: 40-50 Mpa, and flexural strength: 66-75 Mpa) reported by other companies prepared with their own ROMP catalysts in Japan and USA, which advantage in the present invention will provide an alternative method of making high-quality of PDCPD material for broad uses in polymer industry.

Equation 7:

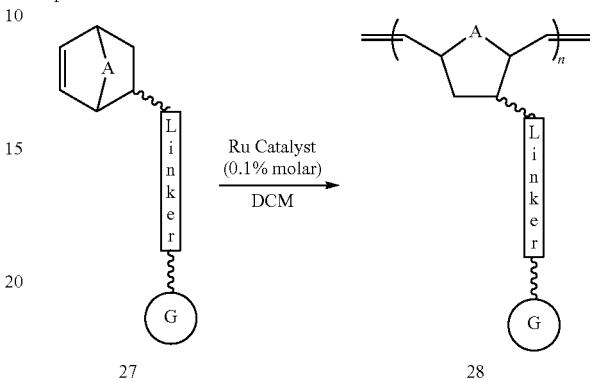

Some selected structure of prepared polymers 28a-28g is listed as follows, and ROMP results are listed in Table 3:

TABLE 3

Selected ROMP results

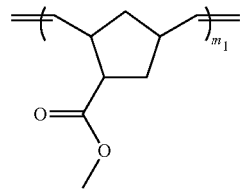

28a

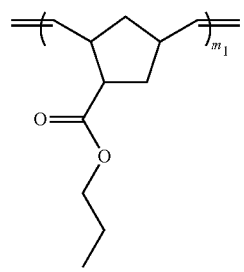

28b

TABLE 3-continued
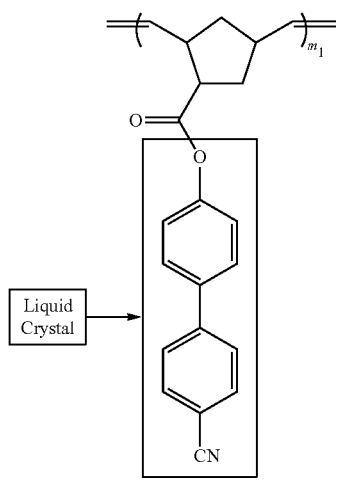
28c
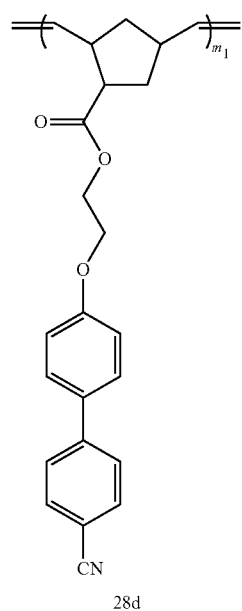
28d

TABLE 3-continued
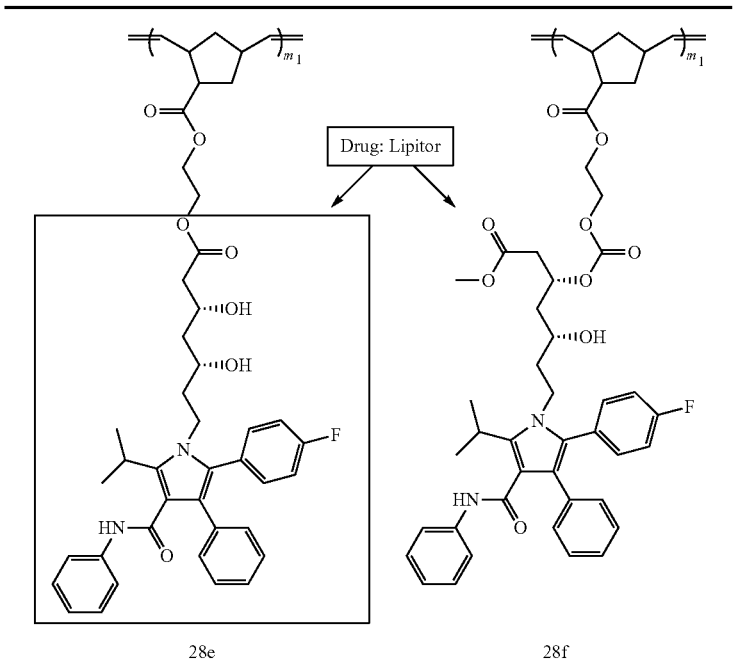
28e     28f
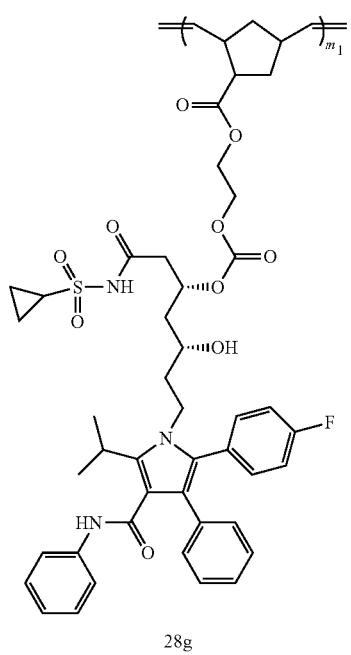
28g
| SM | Amount (g) | Solvent | Catalyst (0.1%) | Yield (%) | Polymer | Appearance |
|---|---|---|---|---|---|---|
| 27a | 0.5 | DCM | 4d | 90 | 28a | white solid |
| 27b | 0.5 | DCM | 4d | 93 | 28b | white solid |
| 27c | 0.5 | DCM | 4d | 97 | 28c | white solid |
| 27d | 0.5 | DCM | 4d | 95 | 28d | white solid |
| 27e | 0.5 | DCM | 4d | 93 | 28e | white solid |
| 27f | 0.5 | DCM | 4d | 81 | 28f | white solid |
| 27g | 0.5 | DCM | 4d | 87 | 28g | white solid |

The results of Table 3 show that, small molecule liquid crystal or pro-drug monomer can react with new Ru catalysts selected from the present invention to form polymerized macromolecule liquid crystal (28c and 28d) and polymer-linked prodrugs (28e, 28f and 28g) with special properties and applications. The results of activity test show that several new catalysts (such as 4d, 4f, 6g and 11a) of the present invention have better catalytic activity for olefin monomers (27a-27g), and the ROMP reactions were completed in 5-15 hrs. Yield is better than 80% with optimized polymerization conditions in the presence of new Ru catalyst 4d.

The results of polymerization test show that different Ru catalysts of the present invention have significantly different activity and selectivity for different cyclo-olefin monomers. In particular, some new Ru catalysts (e.g., 4d and 6g) have lower catalytic activities in RCM reaction, but have very good activity in ROMP reactions, which demonstrates that several new Ru catalysts in the present invention have the high selectivity and catalytic activity for ROMP and RCM, respectively.

Equation 8:

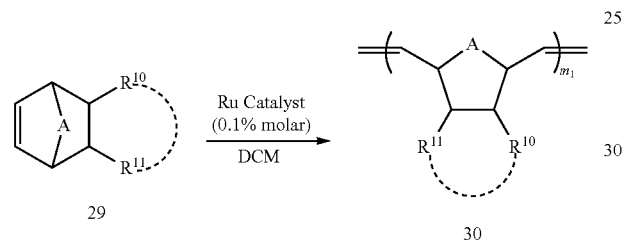

Some selected structure of prepared polymers 30a-30n is listed as follows, and some selected ROMP results are listed in Table 4:

TABLE 4

Selected ROMP results

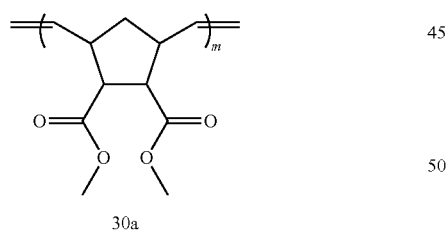

30a

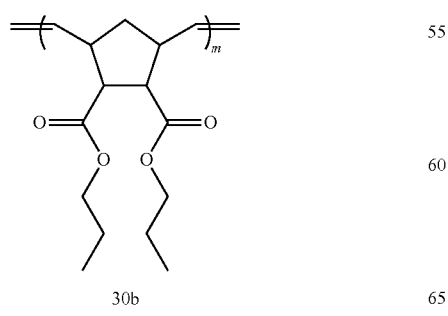

30b

TABLE 4-continued

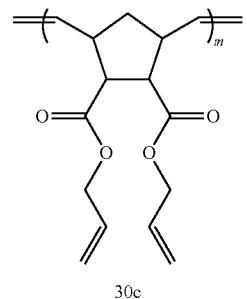

30c

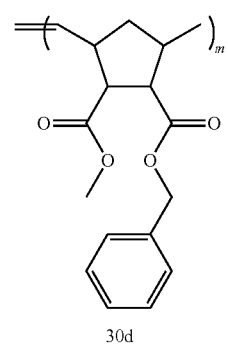

30d

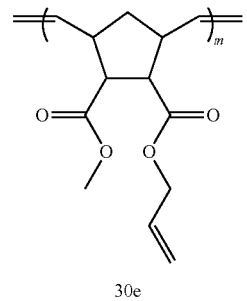

30e

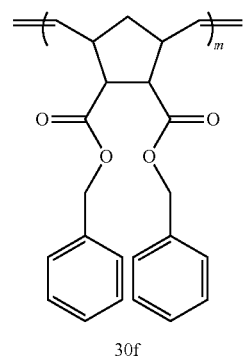

30f

TABLE 4-continued

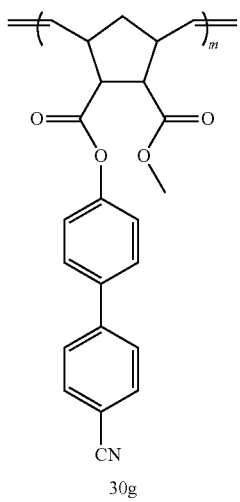

30g

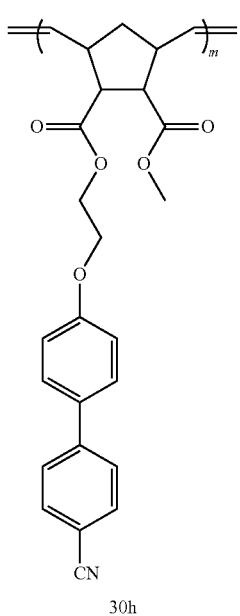

30h

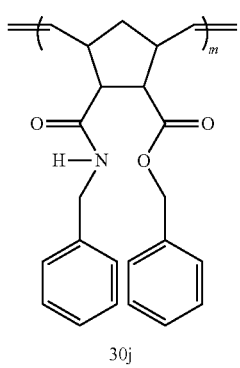

30j

TABLE 4-continued

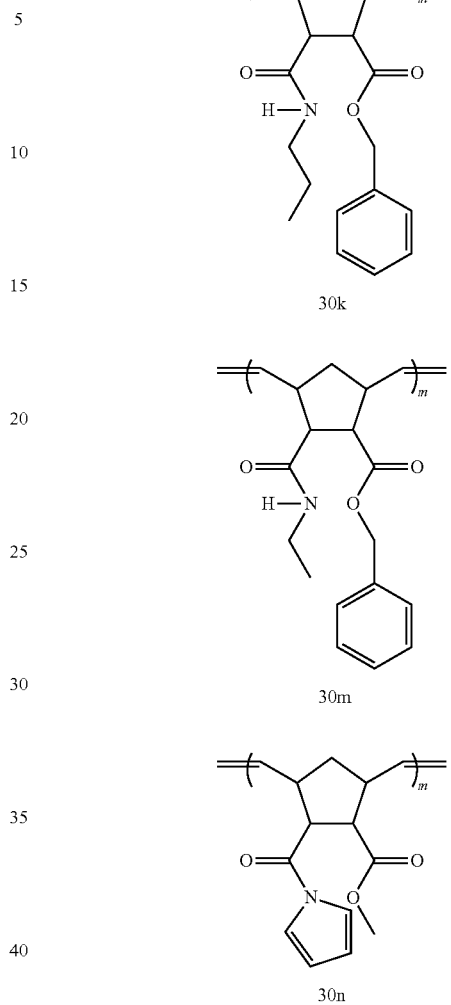

| SM | Amount (g) | Solvent | Catalyst (0.1%) | Yield (%) | Polymer | Appearance |
|---|---|---|---|---|---|---|
| 29a | 0.5 | DCM | 4d | 75 | 30a | white solid |
| 29b | 0.5 | DCM | 4d | 90 | 30b | white solid |
| 29c | 0.5 | DCM | 4d | 71 | 30c | white solid |
| 29d | 0.5 | DCM | 4d | 60 | 30d | white solid |
| 29e | 0.5 | DCM | 6g | 46 | 30e | white solid |
| 29f | 0.5 | DCM | 4d | 85 | 30f | white solid |
| 29g | 0.5 | DCM | 4d | 97 | 30g | white solid |
| 29h | 0.5 | DCM | 4d | 98 | 30h | white solid |
| 29j | 0.5 | DCM | 4d | 97 | 30j | white solid |
| 92k | 0.5 | DCM | 4d | 96 | 30k | white solid |
| 29m | 0.5 | DCM | 4d | 95 | 30m | white solid |
| 29n | 0.5 | DCM | 4d | 93 | 30n | white solid |

The results in Table 4 show that most of cyclo-olefin monomers with different functional groups (29a-29n) were polymerized in the presence of new Ru catalysts such as 4d or 6g selected from the present invention to form functional polymers with different chemical and physical properties.

Equation 9:
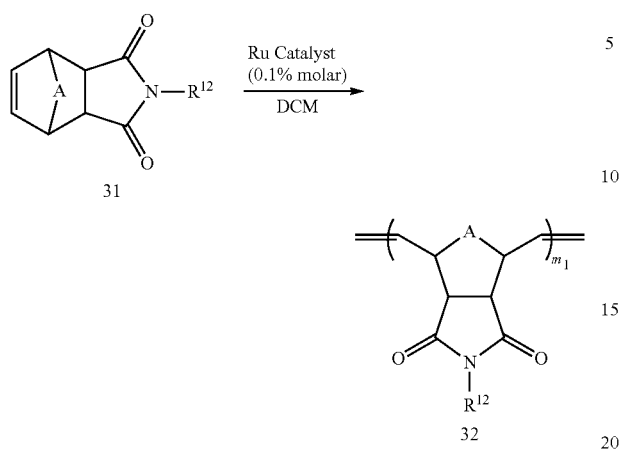
Some selected structure of prepared polymers 32a-32m is listed as follows, and some selected ROMP results are listed in Table 5:
TABLE 5
Selected ROMP results
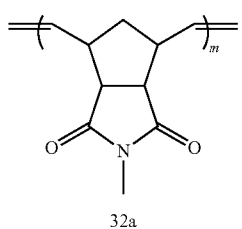
32a
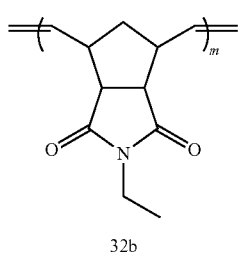
32b
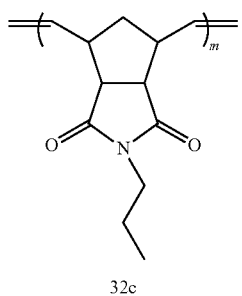
32c
TABLE 5-continued
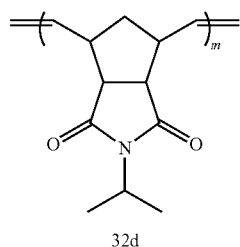
32d
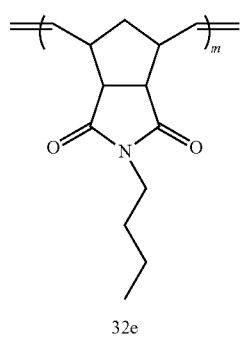
32e
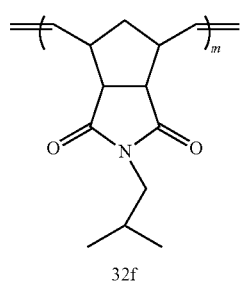
32f
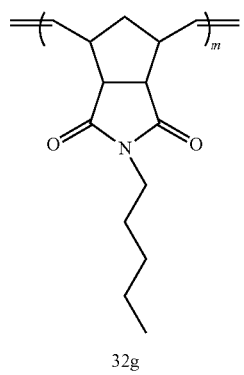
32g
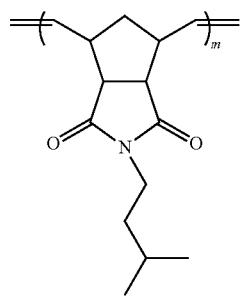
32h

TABLE 5-continued

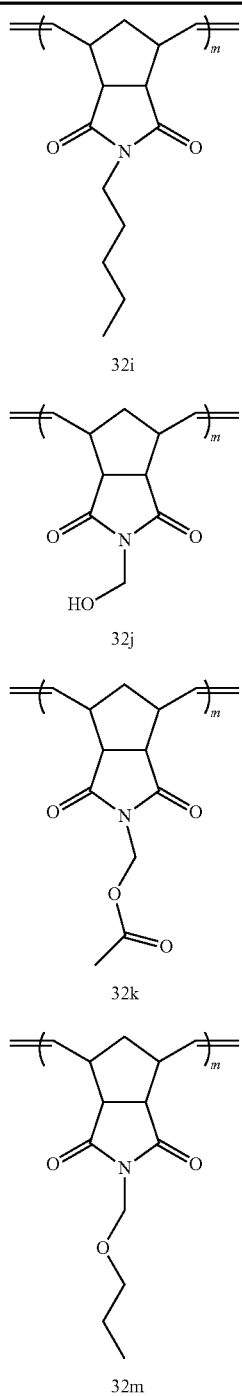

| SM | Amount (g) | Solvent (mL) | Catalyst (0.1%) | Yield (%) | Polymer | Appearance |
|---|---|---|---|---|---|---|
| 31a | 0.5 | DCM | 4d | 96 | 32a | white solid |
| 31b | 0.5 | DCM | 4d | 92 | 32b | white solid |
| 31c | 0.5 | DCM | 4d | 92 | 32c | white solid |
| 31d | 0.5 | DCM | 4d | 89 | 32d | white solid |
| 31e | 0.5 | DCM | 4d | 91 | 32e | white solid |
| 31f | 0.5 | DCM | 4d | 87 | 32f | white solid |
| 31g | 0.5 | DCM | 4d | 91 | 32g | white solid |
| 31h | 0.5 | DCM | 4d | 85 | 32h | white solid |
| 31i | 0.5 | DCM | 4d | 87 | 32i | white solid |
| 31j | 0.5 | DCM | 4d | 97 | 32j | white solid |
| 31k | 0.5 | DCM | 4d | 87 | 34k | white solid |
| 31m | 0.5 | DCM | 4d | 98 | 32m | white solid |

The results in Table 5 show that hat most of cyclo-olefin monomers with different functional groups (31a-31m) were polymerized in the presence of new Ru catalyst 4d selected from the present invention to form functional polymers with different chemical and physical properties. Moreover, several products 32a, 32b, 32c, and 34m could be used to form film with high strength (over 50 Mpa).

Based on the activity studies in equations 1-9 and Tables (1-1, 1-2, 1-3, 1-4, 1-5 and 2), it is found that some of novel Ru catalysts such as 4d, 4f, 4g, 4ab, 6g, 6h, 8g, 8h, 10c and 10d have much better activity and selectivity than other tested and reported metathesis catalysts for the ROMP and RCM reactions, respectively. Moreover, it is found that the electronic effect of multi-substituted benzylidene ligands on the activity and selectivity of Ru complexes is one of the most important factors for the development of new active and selective metathesis catalysts for ROMP and RCM reactions. Based on the intensive study, the present invention provides some useful methods of carrying out either ROMP or RCM reaction with one or two more mixed of novel active Ru catalysts for preparation of some functional polymers linked with small molecule prodrugs and/or pharmaceutical intermediates, respectively.

EXAMPLES

General:

Infrared (IR) spectra were recorded on a Fourier Transform AVATAR™ 360 E.S.P™ spectrophotometer (Unit: cm$^{-1}$). Bands are characterized as broad (br), strong (s), medium (m), and weak (w). $^1$H NMR spectra were recorded on a Varian-400 (400 MHz) spectrometer. Chemical shifts are reported in ppm from tetramethylsilane with the solvent resonance as the internal standard (CDCl$_3$: 7.26 ppm). Data are reported as follows: chemical shift, multiplicity (s=singlet, d=doublet, t=triplet, q=quartet, br=broad, m=multiplet), coupling constants (Hz), integration, and assignment. $^{19}$F and $^{31}$P NMR spectra were recorded on a Varian-400 (400 MHz) and Gemini-2000 (300 MHz) spectrometers. The chemical shifts of the fluoro resonances were determined relative to trifluoroacetic acid as the external standard (CF$_3$CO$_2$H, 0.00 ppm), and the chemical shifts of the phosphorus resonances were determined relative to phosphoric acid as the external standard (H$_3$PO$_4$: 0.00 ppm). Mass spectra were obtained at Thermo Finnigan LCQ Advantage. Unless otherwise noted, all reactions were conducted in oven- (135° C.) and flame-dried glassware with vacuum-line techniques under an inert atmosphere of dry Ar. THF and Et$_2$O were distilled from sodium metal dried flask, DCM, pentane, and hexanes were distilled from calcium hydride. Different substituted 2-alkoxystyrene ligands were prepared according to literature procedures as shown in Schemes 1-3. Most chemicals were obtained from commercial sources and confirmed to be used without any quality problems. All product purification was performed with silica gel 60 (200-400 mesh) obtained from Qingdao Haiyang Chemical Co. General procedures for preparation of different Ru complexes are described in examples 1 and 2, respectively. General procedures for evaluation of the RCM and ROMP reactions are described in examples 104-107, respectively.

Example 1

Synthesis of Ru Complex 4a ($H_2$IMes)(PCy$_3$)Cl$_2$Ru=CHPh (formula 1b, 860 mg, 1.0 mmol) and CuCl (270 mg, 2.5 mmol, 2.5 eq) were added into a 100 mL of two-neck round-bottom flask filled with inert gas (Ar), and followed by adding DCM (15 mL) and ligand 3a (250 mg, 1.2 mmol, 1.2 eq) into the DCM solution at 20-25° C. The reaction was stirred until completed in 30-60 min. (monitored by TLC). The reaction mixture was filtered and concentrated, then purified by flash column eluting with a gradient solvent (Pentane/DCM 2/1 to DCM). The purified solid product was washed with methanol, and dried under vacuum to obtain 27 mg of green solid product 4a, yield: 4%. The green product was confirmed by $^1$HNMR.

Ru complex (4a) $^1$HNMR (400 MHz, CDCl$_3$): δ 19.09 (s, 1H, Ru=CH), 7.51-6.70 (m, 13H), 5.31 (m, 1H), 4.30 (d, J=12.9 Hz, 1H), 4.04 (s, 4H, NCH$_2$CH$_2$N), 3.61 (d, J=12.9 Hz, 1H), 2.45 (s, 12H), 2.33 (s, 6H).

Example 2

Synthesis of Ru Complex 4b (PCy$_3$)$_2$Cl$_2$Ru=CHPh (formula 1a, 830 mg, 1.0 mmol) and CuCl (270 mg, 2.5 mmol, 2.5 eq) were added into a 100 mL of two-neck round-bottom flask filled with inert gas (Ar), and followed by adding DCM (15 mL) and ligand 3b (250 mg, 1.2 mmol, 1.2 eq) into the DCM solution at 20-25° C. The reaction was stirred until completed in 30-60 min. (monitored by TLC). The reaction mixture was filtered and concentrated, then purified by flash column eluting with a gradient solvent (Pentane/DCM 2/1 to DCM). The purified solid product was washed with methanol, and dried under vacuum to obtain 195 mg of green solid product 4b, yield: 29%. The green product was confirmed by $^1$HNMR.

Ru complex (4b) $^1$HNMR (400 MHz, CDCl$_3$): δ 19.31 (d, J=8.4 Hz, Ru=CH), 7.57-7.50 (m, 4H), 7.31-7.29 (m, 1H), 7.15 (d, J=5.6 Hz, 1H), 6.84-6.81 (m, 2H), 5.78 (d, J=12.0 Hz, 1H), 3.71 (s, 3H), 3.62 (d, J=12.0 Hz, 1H), 2.51 (s, 3H), 2.22-1.13 (m, 33H, PCy$_3$).

Example 3

Synthesis of Ru Complex 4c

The synthetic procedure is the same as in Example 1 in 1.0 mmol scale. 35 mg of green solid product 4c was obtained (yield: 5%).

Ru complex (4c) $^1$HNMR (400 MHz): δ 19.09 (s, 1H, Ru=CH), 7.50-6.69 (m, 12H), 5.27 (m, 1H), 4.33 (d, J=12.9 Hz, 1H), 4.04 (s, 4H, NCH$_2$CH$_2$N), 3.59 (d, J=12.9 Hz, 1H), 2.45 (s, 12H), 2.37 (s, 6H).

Example 4

Synthesis of Ru Complex 4d

The synthetic procedure is the same as in Example 1 in 1.0 mmol scale. 231 mg of green solid product 4d was obtained (yield: 32%).

Ru complex (4d) $^1$HNMR (400 MHz, CDCl$_3$): δ 18.68 (s, Ru=CH), 7.23-6.65 (m, 10H), 6.36 (dd, J=2.8, 9.6 Hz, 1H), 6.03 (d, J=12.8 Hz, 1H), 4.14-3.90 (m, 4H, NCH$_2$CH$_2$N), 3.85 (s, 3H), 3.47 (d, J=12.8 Hz, 1H), 2.89-1.62 (m, 18H).

Example 5

Synthesis of Ru Complex 4e

The synthetic procedure is the same as in Example 2 in 1.0 mmol scale. 243 mg of green solid product 4e was obtained (35% yield).

Ru complex (4e) $^1$HNMR (400 MHz, CDCl$_3$): δ 19.28 (d, J=8.4 Hz, Ru=CH), 7.45 (d, J=8.8 Hz, 2H), 7.31-7.16 (m, 3H), 6.83 (d, J=8.8 Hz, 2H), 5.13 (t, J=12.4 Hz, 1H), 7.96 (d, J=12.4 Hz, 1H), 3.85 (d, J=12.4 Hz, 1H), 3.80 (s, 3H), 2.28-1.24 (m, 33H, PCy$_3$).

Example 6

Synthesis of Ru Complex 4f

The synthetic procedure is the same as in Example 1 in 1.0 mmol scale. 103 mg of green solid product 4f was obtained (yield: 14%).

Ru complex (4h) $^1$HNMR (400 MHz, CDCl$_3$): δ 18.99 (s, Ru=CH), 7.48-7.44 (m, 1H), 7.19-6.86 (m, 7H), 6.72-6.66 (m, 1H), 5.29 (t, J=13.2 Hz, 1H), 4.19-3.58 (m, 8H), 2.52-2.37 (m, 18H).

Example 7

Synthesis of Ru Complex 4g

The synthetic procedure is the same as in Example 1 in 1.0 mmol scale. 61 mg of green solid product 4g was obtained (yield: 8%).

Ru complex (4g) $^1$HNMR (400 MHz, CDCl$_3$): δ 19.11 (s, 1H, Ru=CH), 8.36 (dd, J=2.0, 8.0 Hz, 1H), 7.29-6.65 (m, 10H), 5.30 (t, J=13.6 Hz, 1H), 4.23 (d, J=13.2 Hz, 1H), 4.10 (s, 3H), 3.80 (s, 4H, NCH$_2$CH$_2$N), 3.69 (d, J=13.2 Hz, 1H), 2.65-2.08 (m, 18H).

Example 8

Synthesis of Ru Complex 4h

The synthetic procedure is the same as in Example 1 in 1.0 mmol scale. 315 mg of green solid product 4h was obtained (yield: 42%).

Ru complex (4h) $^1$HNMR (400 MHz, CDCl$_3$): 19.02 (s, 1H, Ru=CH), 7.21-6.82 (m, 8H), 6.40 (dd, J=9.6 Hz, 1.6 Hz), 5.21 (m, 1H), 4.06-4.00 (m, 5H), 3.70 (s, 3H), 3.54 (d, J=13.2 Hz, 1H), 2.48-2.18 (m, 24H).

Example 9

Synthesis of Ru Complex 4j

The synthetic procedure is the same as in Example 1 in 1.0 mmol scale. 353 mg of green solid product 4j was obtained (yield: 48%).

Ru complex (4j) $^1$H-NMR (400 MHz, CDCl$_3$): δ 18.88 (s, 1H, Ru=CH), 7.57-6.44 (m, 11H), 5.36 (t, J=13.2 Hz, 1H), 4.16-4.02 (m, 5H), 4.01 (d, J=13.2 Hz, 1H), 2.75-2.00 (m, 19H), 1.01-0.90 (m, 6H).

Example 10

Synthesis of Ru Complex 4k

The synthetic procedure is the same as in Example 1 in 1.0 mmol scale. 490 mg of green solid product 4k was obtained (yield: 68%).

Ru complex (4k) $^1$HNMR (400 MHz, CDCl$_3$): δ 18.90 (s, 1H, Ru=CH), 7.27-6.77 (m, 9H), 6.41 (d, J=8.0 Hz, 1H), 5.43 (t, J=13.2 Hz, 1H), 4.18-4.00 (m, 5H), 3.25 (d, J=13.6 Hz, 1H), 2.76-1.27 (m, 24H).

Example 11

Synthesis of Ru Complex 4m

The synthetic procedure is the same as in Example 1 in 1.0 mmol scale. 404 mg of green solid product 4m was obtained (yield: 52%).

Ru complex (4m) $^1$HNMR (400 MHz, CDCl$_3$): δ 18.95 (s, 1H, Ru=CH), 7.43-6.36 (m, 10H), 4.00 (m, 6H), 2.67-2.06 (m, 20H), 0.90-0.83 (m, 12H).

Example 12

Synthesis of Ru Complex 4n

The synthetic procedure is the same as in Example 1 in 1.0 mmol scale. 470 mg of green solid product 4n was obtained (yield: 64%).

Ru complex (4n): $^1$H-NMR (400 MHz, CDCl$_3$): δ 18.88 (s, 1H, Ru=CH), 7.25-6.36 (m, 9H), 5.40 (t, J=13.2 Hz, 1H), 4.14-4.00 (m, 6H), 2.77-1.90 (m, 27H).

Example 13

Synthesis of Ru Complex 4p

The synthetic procedure is the same as in Example 1 in 1.0 mmol scale. 184 mg of green solid product 4p was obtained (yield: 26%).

Ru complex (4p) $^1$HNMR (400 MHz, CDCl$_3$): δ 18.91 (s, 1H, Ru=CH), 7.63-6.42 (m, 10H), 5.27 (t, J=13.2 Hz, 1H), 4.13-4.01 (m, 5H), 3.44 (d, J=13.2 Hz, 1H), 2.46-2.00 (m, 21H).

Example 14

Synthesis of Ru Complex 4q

The synthetic procedure is the same as in Example 1 in 1.0 mmol scale. 291 mg of green solid product 4q was obtained (yield: 38%).

Ru complex (4q) $^1$HNMR (400 MHz, CDCl$_3$): δ 18.75 (s, 1H, Ru=CH), 7.26-6.21 (m, 9H), 4.05-3.85 (m, 5H), 3.72 (s, 3H), 3.34 (d, J=13.2 Hz, 1H), 2.82-0.95 (m, 30H).

Example 15

Synthesis of Ru Complex 4r

The synthetic procedure is the same as in Example 1 in 1.0 mmol scale. 101 mg of green solid product 4r was obtained (yield: 14%).

Ru complex (4r) $^1$HNMR (400 MHz, CDCl$_3$): δ 18.89 (s, 1H, Ru=CH), 7.69-6.43 (m, 10H), 5.23 (dd, J=13.2, 11.3 Hz, 1H), 4.16-3.94 (m, 5H), 3.46 (d, J=11.3 Hz, 1H), 2.62-1.00 (m, 21H).

Example 16

Synthesis of Ru Complex 4s

The synthetic procedure is the same as in Example 1 in 1.0 mmol scale. 679 mg of green solid product 4s was obtained (yield: 85%).

Ru complex (4s) $^1$HNMR (400 MHz, CDCl$_3$): δ 18.68 (s, 1H, Ru=CH), 7.28-6.42 (m, 10H), 6.37 (d, J=8.5 Hz, 1H), 5.05 (m, 1H), 4.06-3.93 (m, 7H), 3.57 (d, J=12.8 Hz, 1H), 2.89-1.29 (m, 29H).

Example 17

Synthesis of Ru Complex 4t

The synthetic procedure is the same as in Example 1 in 1.0 mmol scale. 185 mg of green solid product 4t was obtained (yield: 23%).

Ru complex (4t) $^1$HNMR (300 MHz, CDCl$_3$): δ 18.97 (s, 1H, Ru=CH), 8.54-8.45 (m, 2H), 6.66-6.96 (m, 8H), 4.16-4.10 (m, 1H), 4.03 (s, 4H, NCH$_2$CH$_2$N), 2.63-1.75 (m, 22H), 0.92 (d, J=7.6 Hz), 0.83 (d, J=7.6 Hz).

Example 18

Synthesis of Ru Complex 4u

The synthetic procedure is the same as in Example 1 in 1.0 mmol scale. 254 mg of green solid product 4u was obtained (yield: 32%).

Ru complex (4u) $^1$HNMR (300 MHz, CDCl$_3$): δ 19.03 (s, 1H, Ru=CH), 7.48-6.63 (m, 10H), 5.53 (m, 1H), 4.81-4.78 (m, 1H), 4.00 (s, 4H, NCH$_2$CH$_2$N), 2.51-2.49 (m, 1H), 2.51-2.32 (m, 18H), 1.12 (d, J=7.6 Hz), 1.04 (d, J=7.6 Hz).

Example 19

Synthesis of Ru Complex 4v

The synthetic procedure is the same as in Example 1 in 1.0 mmol scale. 73 mg of green solid product 4v was obtained (yield: 10%).

Ru complex (4v) $^1$HNMR (400 MHz, CDCl$_3$): δ 18.97 (s, Ru=CH), 7.50-6.58 (m, 11H), 5.26-3.52 (m, 8H), 3.48-2.07 (m, 18H), 1.23 (d, J=6.4 Hz, 6H).

Example 20

Synthesis of Ru Complex 4w

The synthetic procedure is the same as in Example 2 in 1.0 mmol scale. 219 mg of green solid product 4w was obtained (yield: 31%).

Ru complex (4w) $^1$HNMR (400 MHz, CDCl$_3$): δ 19.56 (d, J=9.9 Hz, Ru=CH), 8.20 (d, J=8.1 Hz, 1H), 7.66-6.84 (m, 6H), 5.46 (d, J=12 Hz, 1H), 5.22 (t, J=6 Hz, 1H), 4.56 (m, 1H), 3.95 (d, J=12.0 Hz, 1H), 2.34-0.87 (m, 39H, PCy$_3$).

Example 21

Synthesis of Ru Complex 4x

The synthetic procedure is the same as in Example 2 in 1.0 mmol scale. 420 mg of green solid product 4x was obtained (yield: 58%).

Ru complex (4x) $^1$HNMR (400 MHz, CDCl$_3$): δ 19.55 (d, J=9.9 Hz, Ru=CH), 8.14 (d, J=8.1 Hz, 1H), 7.36-6.83 (m, 6H), 5.46 (d, J=12.0 Hz, 1H), 5.13 (t, J=6.0 Hz, 1H), 4.56 (m, 1H), 3.90 (d, J=12.0 Hz, 1H), 2.30-1.25 (m, 39H, PCy$_3$).

Example 22

Synthesis of Ru Complex 4y

The synthetic procedure is the same as in Example 1 in 1.0 mmol scale. 267 mg of green solid product 4y was obtained (yield: 37%).
Ru complex (4y): $^1$HNMR (400 MHz, CDCl$_3$): δ 18.83 (s, Ru=CH), 7.50-6.39 (m, 11H), 5.21 (t, J=12.4 Hz, 1H), 4.69-3.46 (m, 9H), 2.62-2.08 (m, 18H).

Example 23

Synthesis of Ru Complex 4z

The synthetic procedure is the same as in Example 2 in 1.0 mmol scale. 362 mg of green solid product 4z was obtained (yield: 52%).
Ru complex (4z) $^1$HNMR (400 MHz, CDCl$_3$): δ 19.35 (d, J=9.9 Hz, Ru=CH), 8.11 (d, J=8.1 Hz, 1H), 7.34-6.85 (m, 6H), 5.48 (d, J=12.0 Hz, 1H), 5.27 (t, J=6 Hz, 1H), 3.93 (d, J=12.0 Hz, 1H), 3.88 (s, 3H), 2.33-1.24 (m, 3H, PCy$_3$).

Example 24

Synthesis of Ru Complex 4aa

The synthetic procedure is the same as in Example 1 in 1.0 mmol scale. 631 mg of green solid product 4aa was obtained (yield: 84%).
Ru complex (4aa) $^1$HNMR (400 MHz, CDCl$_3$): δ 18.89 (s, Ru=CH), 7.60-6.45 (m, 11H), 5.13-3.52 (m, 8H), 2.95-2.10 (m, 18H), 0.95 (d, J=6.4 Hz, 6H)

Example 25

Synthesis of Ru Complex 4ab

The synthetic procedure is the same as in Example 1 in 1.0 mmol scale. 300 mg of green solid product 4ab was obtained (yield: 40%).
Ru complex (4ab) $^1$HNMR (400 MHz, CDCl$_3$): δ 16.52 (s, Ru=CH), 7.58 (m, 1H), 7.09 (s, 4H), 6.93-6.60 (m, 6H), 4.52 (m, 1H), 4.35 (s, 2H), 4.18 (s, 4H, NCH$_2$CH$_2$N), 3.89 (s, 6H), 2.49 (s, 12H), 2.40 (s, 6H).

Example 26

Synthesis of Ru Complex 4ac

The synthetic procedure is the same as in Example 1 in 1.0 mmol scale. 367 mg of green solid product 4ac was obtained (yield: 50%).
Ru complex (4ac) $^1$HNMR (400 MHz, CDCl$_3$): δ 19.03 (s, Ru=CH), 8.38 (d, J=2.0 Hz, 1H), 7.69 (d, J=16.0 Hz, 1H), 7.44 (d, J=7.6 Hz, 1H), 7.21-7.03 (m, 5H), 6.83-6.59 (m, 3H), 5.24 (t, J=12.0 Hz, 1H), 4.66 (d, J=12.0 Hz, 1H), 4.45 (m, 1H), 4.20-4.05 (m, 4H, NCH$_2$CH$_2$N), 3.62 (d, J=12.0 Hz, 1H), 2.69-2.03 (m, 18H), 1.18 (d, J=5.6 Hz, 6H).

Example 27

Synthesis of Ru Complex 4ad

The synthetic procedure is the same as in Example 1 in 1.0 mmol scale. 374 mg of green solid product 4ad was obtained (yield: 49%).

Ru complex (4ad) $^1$HNMR (400 MHz, CDCl$_3$): δ 16.52 (s, Ru=CH), 7.59 (m, 1H), 7.09 (s, 4H), 6.92-6.84 (m, 4H), 6.75-6.66 (m, 2H), 4.59 (m, 1H), 4.35 (s, 2H), 4.18 (s, 4H, NCH$_2$CH$_2$N), 3.89 (s, 3H), 2.49 (s, 12H), 2.40 (s, 6H, 18H), 0.93 (m, 6H).

Example 28

Synthesis of Ru Complex 4ae

The synthetic procedure is the same as in Example 1 in 1.0 mmol scale. 389 mg of green solid product 4ae was obtained (yield: 50%).
Ru complex (4ae) $^1$HNMR (400 MHz, CDCl$_3$): δ 19.03 (s, 1H, Ru=CH), 8.38 (d, J=2.0 Hz, 1H), 7.69 (d, J=16.0 Hz, 1H), 7.44 (d, J=7.6 Hz, 1H), 7.21-7.03 (m, 5H), 6.83-6.59 (m, 3H), 5.24 (t, J=12.0 Hz, 1H), 4.66 (d, J=12.0 Hz, 1H), 4.45 (m, 1H), 4.20-4.05 (m, 4H, NCH$_2$CH$_2$N), 3.62 (d, J=12.0 Hz, 1H), 2.69-2.03 (m, 18H), 1.18 (d, J=5.6 Hz, 6H).

Example 29

Synthesis of Ru Complex 4af

The synthetic procedure is the same as in Example 1 in 1.0 mmol scale. 111 mg of green solid product 4af was obtained (yield: 15%).
Ru complex (40) $^1$HNMR (400 MHz, CDCl$_3$): δ 18.54 (s, 1H, Ru=CH), 7.45 (d, J=8.0 Hz, 1H), 7.24-7.19 (m, 4H), 7.06-6.96 (m, 6H), 6.14 (d, J=13.2 Hz, 1H), 5.39 (d, J=13.2 Hz, 1H), 4.07-3.77 (m, 7H), 3.52 (s, 3H), 2.65-2.30 (m, 18H).

Example 30

Synthesis of Ru Complex 4ag

The synthetic procedure is the same as in Example 1 in 1.0 mmol scale. 302 mg of green solid product 4ag was obtained (40% yield).
Ru complex (4ag) $^1$HNMR (400 MHz, CDCl$_3$): δ 18.83 (s, 1H, Ru=CH), 7.36-6.14 (m, 10H), 5.12 (t, J=12.4 Hz, 1H), 4.50-3.42 (m, 12H), 2.62-2.05 (m, 18H).

Example 31

Synthesis of Ru Complex 4ah

The synthetic procedure is the same as in Example 1 in 1.0 mmol scale. 376 mg of green solid product 4ah was obtained (yield: 51%).
Ru complex (4ah) $^1$HNMR (400 MHz, CDCl$_3$): δ 18.90 (s, 1H, Ru=CH), 7.60-6.36 (m, 10H), 5.25 (t, J=12.0 Hz, 1H), 4.78 (d, J=12.0 Hz, 1H), 4.05 (s, 4H, NCH$_2$CH$_2$N), 3.53 (s, 3H), 3.43 (d, J=12.0 Hz, 1H), 2.56-2.13 (m, 21H).

Example 32

Synthesis of Ru Complex 4aj

The synthetic procedure is the same as in Example 2 in 1.0 mmol scale. 390 mg of green solid product 4aj was obtained (yield: 55%).
Ru complex (4aj) $^1$HNMR (400 MHz, CDCl$_3$): 819.45 (d, J=9.6 Hz, Ru=CH), 8.18 (d, J=7.6 Hz, 1H), 7.40-7.33 (m, 2H), 7.21-7.11 (m, 2H), 6.95-6.88 (m, 2H), 5.52 (m, 1H), 5.23 (m, 1H), 4.16-3.94 (m, 3H), 2.36-0.81 (m, 36H, PCy$_3$).

Example 33

Synthesis of Ru Complex 4ak

The synthetic procedure is the same as in Example 1 in 1.0 mmol scale. 299 mg of green solid product 4ak was obtained (yield: 37%).

Ru complex (4ak) $^1$HNMR (400 MHz, CDCl$_3$): δ 19.08 (s, 1H, Ru=CH), 7.97-6.33 (m, 10H), 5.08 (m, 2H), 4.34 (m, 1H), 4.02 (s, 4H, NCH$_2$CH$_2$N), 3.41 (m, 1H), 2.53-2.31 (m, 18H), 1.29 (s, 9H), 0.89-0.87 (m, 6H).

Example 34

Synthesis of Ru Complex 4 am

The synthetic procedure is the same as in Example 1 in 1.0 mmol scale. 437 mg of green solid product 4 am was obtained (yield: 54%).

Ru complex (4am) $^1$HNMR (400 MHz, CDCl$_3$): δ 18.85 (s, 1H, Ru=CH), 7.26-6.07 (m, 10H), 5.04 (t, J=13.2 Hz, 1H), 4.48 (m, 1H), 4.39-4.33 (m, 2H), 4.15-4.02 (m, 4H, NCH$_2$CH$_2$N), 3.65 (m, 1H), 2.66-2.05 (m, 18H), 1.55 (m, 6H), 1.38 (m, 6H).

Example 35

Synthesis of Ru Complex 4an

The synthetic procedure is the same as in Example 1 in 1.0 mmol scale. 359 mg of green solid product 4an was obtained (yield: 46%).

Ru complex (4an) $^1$HNMR (400 MHz, CDCl$_3$): δ 18.98 (s, 1H, Ru=CH), 7.66-6.39 (m, 10H), 5.17 (t, J=13.2 Hz, 1H), 4.71 (d, J=13.2 Hz, 1H), 4.36 (m, 1H), 4.06 (brs, 4H, NCH$_2$CH$_2$N), 3.42 (d, J=13.2 Hz, 1H), 2.63-2.09 (m, 21H), 1.09 (m, 6H).

Example 36

Synthesis of Ru Complex 4ap

The synthetic procedure is the same as in Example 1 in 1.0 mmol scale. 380 mg of green solid product 4ap was obtained (yield: 44%).

Ru complex (4ap) $^1$HNMR (400 MHz, CDCl$_3$): δ 18.99 (s, 1H, Ru=CH), 7.45-6.36 (m, 9H), 5.05 (m, 2H), 3.98-3.91 (m, 5H), 3.72 (d, J=13.2 Hz, 1H), 2.48-2.34 (m, 19H), 1.45-0.95 (m, 21H).

Example 37

Synthesis of Ru Complex 4aq

The synthetic procedure is the same as in Example 1 in 1.0 mmol scale. 665 mg of green solid product 4aq was obtained (yield: 90%).

Ru complex (4aq) $^1$H-NMR (400 MHz, CDCl$_3$): δ 18.75 (s, 1H, Ru=CH), 7.50-7.44 (m, 2H), 7.04-6.36 (m, 9H), 5.32-5.21 (m, 1H), 4.65 (d, J=13.2 Hz, 1H), 4.16-4.04 (m, 4H, NCH$_2$CH$_2$N), 3.59 (s, 3H), 3.48 (d, J=13.2 Hz, 1H), 2.62-2.32 (m, 18H).

Example 38

Synthesis of Ru Complex 4ar

The synthetic procedure is the same as in Example 1 in 1.0 mmol scale. 499 mg of green solid product 4ar was obtained (yield: 65%).

Ru complex (4ar) $^1$HNMR (300 MHz, CDCl$_3$): δ 18.82 (s, 1H, Ru=CH), 7.47-7.43 (m, 2H), 7.01-6.56 (m, 9H), 5.12-5.09 (m, 1H), 4.56-4.45 (m, 2H), 4.40-4.15 (m, 4H, NCH$_2$CH$_2$N), 3.48-3.45 (m, 1H), 2.64-2.04 (m, 18H), 1.10 (d, J=6.4 Hz, 6H).

Example 39

Synthesis of Ru Complex 4 as

The synthetic procedure is the same as in Example 1 in 1.0 mmol scale. 467 mg of green solid product 4 as was obtained (yield: 59%).

Ru complex (4 as) $^1$HNMR (400 MHz, CDCl$_3$): δ 18.82 (s, 1H, Ru=CH), 8.15 (dd, J=6.4, 1.2 Hz, 2H), 7.51 (d, J=1.2 Hz, 1H), 7.44 (d, J=1.2 Hz, 1H), 7.05-6.99 (m, 5H), 8.15 (d, J=6.4 Hz, 2H), 6.59-6.56 (m, 1H), 5.22 (m, 1H), 4.63 (m, 1H), 4.41 (m, 1H), 3.96 (m, 4H, NCH$_2$CH$_2$N), 3.55-3.52 (m, 1H), 2.66-2.33 (m, 18H), 1.14 (d, J=6.4 Hz, 6H).

Example 40

Synthesis of Ru Complex 4 at

The synthetic procedure is the same as in Example 1 in 1.0 mmol scale. 341 mg of green solid product 4 at was obtained (yield: 42%).

Ru complex (4 at) $^1$HNMR (400 MHz, CDCl$_3$): δ 19.02 (s, 1H, Ru=CH), 7.87 (dd, J=8.0, 1.2 Hz, 1H), 7.44 (dd, J=7.2, 1.2 Hz, 1H), 7.25-7.03 (m, 9H), 5.37-5.30 (m, 1H), 4.76-4.74 (m, 1H), 4.16-4.01 (m, 4H, NCH$_2$CH$_2$N), 3.58-3.54 (m, 4H), 2.75 (s, 6H), 2.73-1.98 (m, 18H).

Example 41

Synthesis of Ru Complex 4au

The synthetic procedure is the same as in Example 1 in 1.0 mmol scale. 471 mg of green solid product 4au was obtained (yield: 51%).

Ru complex (4au) $^1$HNMR (300 MHz, CDCl3): δ 19.06 (s, 1H, Ru=CH), 7.87 (d, J=7.6 Hz, 1H), 7.42 (d, J=7.6 Hz, 1H), 7.29 (d, J=12.0 Hz, 1H), 7.11-6.56 (m, to 8H), 5.22-5.19 (m, 1H), 4.63-4.64 (m, 1H), 4.45-4.42 (m, 1H), 4.14-4.01 (m, 4H, NCH$_2$CH$_2$N), 3.56-3.53 (m, 1H), 3.12-3.07 (m, 4H), 2.67-2.36 (m, 18H), 1.99-1.00 (m, 24H).

Example 42

Synthesis of Ru Complex 4av

The synthetic procedure is the same as in Example 1 in 1.0 mmol scale. 622 mg of green solid product 4av was obtained (yield: 74%).

Ru complex (4av) $^1$HNMR (300 MHz, CDCl$_3$): δ 19.06 (s, 1H, Ru=CH), 7.87 (d, J=7.6 Hz, 1H), 7.42 (d, J=7.6 Hz, 1H), 7.11-6.56 (m, 9H), 5.27-5.20 (m, 1H), 4.64-4.61 (m, 1H), 4.46-4.44 (m, 1H), 4.14-4.01 (m, 4H, NCH$_2$CH$_2$N), 3.59-3.56 (m, 1H), 3.12-3.07 (m, 4H), 2.75 (s, 6H), 2.67-2.36 (m, 18H), 1.13 (d, J=6.0 Hz, 6H).

Example 43

Synthesis of Ru Complex 4aw

The synthetic procedure is the same as in Example 2 in 1.0 mmol scale. 626 mg of green solid product 4aw was obtained (yield: 77%).

Ru complex (4aw) ¹HNMR (400 MHz, CDCl₃): δ 19.56 (d, J=9.6 Hz, Ru=CH), 8.21 (d, J=8.0 Hz, 1H), 8.09 (d, J=2.0 Hz, 1H), 8.10 (dd, J=7.6, 2 Hz, 1H), 7.34-6.87 (m, 4H), 5.47-5.44 (m, 1H), 5.33-5.27 (m, 1H), 4.62-4.56 (m, 1H), 3.99-3.96 (m, 1H), 2.80 (s, 6H), 2.30-1.24 (m, 39H, PCy₃).

Example 44

Synthesis of Ru Complex 4ax

The synthetic procedure is the same as in Example 1 in 1.0 mmol scale. 421 mg of green solid product 4ax was obtained (yield: 47%).

Ru complex (4ax) ¹HNMR (400 MHz, CDCl₃): δ 18.99 (s, 1H, Ru=CH), 7.88 (dd, J=8.0, 2.0 Hz, 1H), 7.44 (dd, J=7.2, 1.2 Hz, 1H), 7.28-6.63 (m, 9H), 5.35-5.28 (m, 1H), 4.75-4.72 (m, 1H), 4.16-4.12 (m, 4H, NCH₂CH₂N), 3.61 (s, 3H), 3.56-3.52 (m, 4H), 3.10-3.06 (m, 4H), 2.63-2.05 (m, 18H), 1.37-0.98 (m, 14H).

Example 45

Synthesis of Ru Complex 4ay

The synthetic procedure is the same as in Example 1 in 1.0 mmol scale. 241 mg of green solid product 4ay was obtained (yield: 27%).

Ru complex (4ay) ¹HNMR (400 MHz, CDCl₃): δ 19.03 (s, 1H, Ru=CH), 7.60 (d, J=7.6 Hz, 1H), 7.43 (d, J=3.6 Hz, 1H), 7.14 (s, 1H), 7.09-7.00 (m, 5H), 6.81-6.57 (m, 3H), 5.22 (m, 1H), 4.64-4.61 (m, 1H), 4.64-4.42 (m, 2H), 4.15-4.02 (m, 4H, NCH₂CH₂N), 3.16 (m, 1H), 3.17 (m, 1H), 2.67-2.00 (m, 18H), 1.85-1.00 (m, 16H).

Example 46

Synthesis of Ru Complex 4ba

The synthetic procedure is the same as in Example 1 in 1.0 mmol scale. 176 mg of green solid product 4ba was obtained (yield: 22%).

Ru complex (4ba) ¹HNMR (400 MHz, CDCl₃): δ 18.74 (s, 1H, Ru=CH), 7.25-7.24 (m, 1H), 7.19 (s, 1H), 7.14-7.04 (m, 7H), 6.93 (s, 1H), 6.71 (s, 1H), 6.41-6.40 (d, J=9.0 Hz, 1H), 6.10-6.07 (d, J=12.0 Hz, 1H), 4.52-4.49 (d, J=13.5 Hz, 1H), 4.33-4.29 (d, J=18.5 Hz, 1H), 4.09 (s, 2H), 3.92 (s, 2H), 3.31 (s, 3H), 2.96-2.92 (d, J=19.0 Hz, 1H), 2.83 (s, 3H), 2.71 (s, 3H), 2.47 (s, 3H), 2.39 (s, 3H), 2.06 (s, 3H), 2.02 (s, 3H).

Example 47

Synthesis of Ru Complex 4bb

The synthetic procedure is the same as in Example 1 in 1.0 mmol scale. 237 mg of green solid product 4bb was obtained (yield: 30%).

Ru complex (4bb) ¹HNMR (400 MHz, CDCl₃): δ 18.74 (s, 1H, Ru=CH), 7.27-7.25 (dd, J=8.0, 3.0 Hz, 1H), 7.19 (s, 1H), 7.14-7.05 (m, 7H), 6.93 (s, 1H), 6.71 (s, 1H), 6.42-6.40 (d, J=9.0 Hz, 1H), 6.07-6.05 (d, J=12.5 Hz, 1H), 4.65-4.61 (m, 1H), 4.51-4.49 (d, J=12.5 Hz, 1H), 4.24-4.20 (d, J=18.0 Hz, 1H), 4.10 (s, 2H), 3.92 (s, 2H), 2.90-2.86 (d, J=18 Hz, 1H), 2.83 (s, 3H), 2.71 (s, 3H), 2.47 (s, 3H), 2.39 (s, 3H), 2.07 (s, 3H), 2.03 (s, 3H), 0.90-0.82 (d, J=33.0, 6.5 Hz, 6H).

Example 48

Synthesis of Ru Complex 4bc

The synthetic procedure is the same as in Example 1 in 1.0 mmol scale. 578 mg of green solid product 4bc was obtained (yield: 73%).

Ru complex (4bc) ¹HNMR (400 MHz, CDCl₃): δ 18.72 (s, 1H, Ru=CH), 7.24-7.22 (dd, J=8.5, 2.5 Hz, 1H), 7.16 (s, 1H), 7.07-7.04 (m, 4H), 6.91 (s, 1H), 6.75 (s, 1H), 6.66 (s, 1H), 6.64 (s, 1H), 6.39-6.38 (d, J=8.0 Hz, 1H), 6.02-6.00 (d, J=12.0 Hz, 1H), 4.64-4.59 (m, 1H), 4.50-4.47 (d, J=13.0 Hz, 1H), 4.13-4.09 (d, J=18 Hz, 1H), 4.08 (s, 2H), 3.90 (s, 2H), 3.83 (s, 3H), 2.81 (s, 3H), 2.81-2.79 (d, J=11.5 Hz, 1H), 2.69 (s, 3H), 2.45 (s, 3H), 2.39 (s, 3H), 2.08 (s, 3H), 2.01 (s, 3H), 0.89-0.81 (dd, J=34.0, 6.0 Hz, 6H).

Example 49

Synthesis of Ru Complex 4bd

The synthetic procedure is the same as in Example 1 in 1.0 mmol scale. 236 mg of green solid product 4bd was obtained (yield: 29%).

Ru complex (4bd) ¹HNMR (400 MHz, CDCl₃): δ 18.72 (s, 1H, Ru=CH), 7.28-7.26 (m, 1H), 7.19 (s, 1H), 7.10-7.05 (m, 6H), 6.94 (s, 1H), 6.82 (s, 1H), 6.41-6.39 (d, J=9.5 Hz, 1H), 6.07-6.04 (d, J=12.0 Hz, 1H), 4.68-4.64 (m, 1H), 4.45-4.43 (d, J=12.5 Hz, 1H), 4.24-4.20 (d, J=18.0 Hz, 1H), 4.09 (s, 2H), 3.93 (s, 2H), 2.91-2.87 (d, J=18.5 Hz, 1H), 2.81 (s, 3H), 2.70 (s, 3H), 2.47 (s, 6H), 2.10 (s, 3H), 2.03 (s, 3H), 0.93-0.87 (dd, J=24.0, 7.0 Hz, 6H).

Example 50

Synthesis of Ru Complex 4be

The synthetic procedure is the same as in Example 1 in 1.0 mmol scale. 396 mg of green solid product 4be was obtained (yield: 49%).

Ru complex (4be) ¹HNMR (400 MHz, CDCl₃): δ 18.71 (s, 1H, Ru=CH), 7.29-7.25 (dd, J=8.5, 2.5 Hz, 1H), 7.19 (s, 1H), 7.13-7.06 (m, 4H), 6.94 (s, 1H), 6.82-6.77 (m, 3H), 6.42-6.39 (dd, J=9.5, 2.5 Hz, 1H), 6.08-6.05 (d, J=13.0 Hz, 1H), 4.66-4.64 (m, 1H), 4.47-4.45 (d, J=12.5 Hz, 1H), 4.21-4.18 (d, J=18 Hz, 1H), 4.10 (s, 2H), 3.93 (s, 2H), 3.89-3.86 (d, J=18 Hz, 1H), 2.83 (s, 3H), 2.70 (s, 3H), 2.48 (s, 3H), 2.42 (s, 3H), 2.11 (s, 3H), 2.02 (s, 3H), 0.92-0.85 (dd, J=26.5, 7.0 Hz, 3H).

Example 51

Synthesis of Ru Complex 4bf

The synthetic procedure is the same as in Example 1 in 1.0 mmol scale. 76 mg of green solid product 4bf was obtained (yield: 10%).

Ru complex (4bf) ¹HNMR (400 MHz, CDCl₃): δ 18.54 (s, 1H, Ru=CH), 7.16-6.87 (m, 7H), 6.15-6.13 (dd, J=10.0, 2.0 Hz, 1H), 5.44-5.41 (d, J=13.5 Hz, 1H), 4.76-4.71 (m, 1H), 4.37-4.34 (d, J=15.5 Hz, 1H), 3.96 (s, 4H, NCH₂CH₂N), 3.07-3.05 (d, J=13 Hz, 1H), 2.75-2.40 (m, 18H), 1.66 (s, 3H), 1.21-1.17 (dd, J=13.0, 6.5 Hz, 6H).

Example 52

Synthesis of Ru Complex 6a

To a 50 mL two-necked round bottom flask, after filling with Ar atmosphere, were added ligand 5a (1.0 mmol) and CuCl (3.0 mmol, 3 eq) and 30 mL dry DCM, followed by refilling with Ar three times and protected with Ar balloon in close system. Ru complex 1b (1.0 mmol) was added under Ar protection, and the mixture was stirred for 0.5 hr at room temperature.

After the reaction was complete, the solution was filtered and the filtrate was concentrated and slurred with silica gel. The crude was obtained by silica gel column chromatography and washed with methanol or pentane-DCM to obtain 453 mg of yellow-green solid product 6a, yield: 79%.

Ru complex (6a) $^1$HNMR (400 MHz, CDCl$_3$): δ 18.53 (s, 1H, Ru=CH), 8.59 (s, 1H), 7.28-6.49 (m, 11H), 4.160 (s, 4H, NCH$_2$CH$_2$N), 2.50 (s, 12H), 2.42 (s, 6H).

Example 53

Synthesis of Ru Complex 6b

To a 50 mL two-necked round bottom flask, after filling with Ar atmosphere, were added ligand 5b (1.0 mmol) and CuCl (3.0 mmol, 3 eq) and 30 mL dry DCM, followed by refilling with Ar three times and protected with Ar balloon in close system. Ru complex 1a (1.0 mmol) was added under Ar protection, and the mixture was stirred for 0.5 hr at room temperature.

After the reaction was complete, the solution was filtered and the filtrate was concentrated and slurred with silica gel. The crude was obtained by silica gel column chromatography and washed with methanol or pentane-DCM to obtain 414 mg yello-green solid product 6b, yield: 77%.

Ru complex (6b) $^1$HNMR (400 MHz, CDCl$_3$): δ 19.20 (d, J=10.8 Hz, Ru=CH), 8.82 (d, J=9.2 Hz, 1H), 7.84 (m, 1H), 7.80 (d, J=8.4 Hz, 1H), 7.45 (m, 4H), 2.46-1.29 (m, 33H, PCy$_3$).

Example 54

Synthesis of Ru Complex 6c

The synthetic procedure is the same as in Example 52 in 1.0 mmol scale. 664 mg of yellow-green solid product 6c was obtained (96% yield).

Ru complex (6c) $^1$HNMR (400 MHz, CDCl$_3$): δ 18.52 (s, 1H, Ru=CH), 8.60 (s, 1H), 7.28-7.13 (m, 7H), 7.02 (d, J=8.8 Hz, 1H), 6.80 (m, 1H), 6.09 (d, J=8.8 Hz, 1H), 4.16 (s, 4H, NCH$_2$CH$_2$N), 3.84 (s, 3H), 2.51 (m, 18H).

Example 55

Synthesis of Ru Complex 6d

The synthetic procedure is the same as in Example 52 in 1.0 mmol scale. 68 mg of yellow-green solid product 6d was obtained (31% yield).

Ru complex (6d): $^1$HNMR (400 MHz, CDCl$_3$): δ 18.73 (s, 1H, Ru=CH), 8.62 (s, 1H), 7.67-7.46 (m, 3H), 7.11 (s, 4H), 6.78-6.65 (m, 5H), 4.13 (s, 4H, NCH$_2$CH$_2$N), to 3.81 (s, 3H), 2.49 (m, 18H).

Example 56

Synthesis of Ru Complex 6e

The synthetic procedure is the same as in Example 52 in 1.0 mmol scale. 41 mg of yellow-green solid product 6e was obtained (24% yield).

Ru complex (6e) $^1$HNMR (400 MHz, CDCl$_3$): δ 18.74 (s, 1H, Ru=CH), 8.60 (s, 1H), 7.69-7.49 (m, 3H), 7.12-7.04 (m, 8H), 6.80 (d, J=8.7 Hz, 1H), 4.13 (s, 4H, NCH$_2$CH$_2$N), 2.50 (m, 18H).

Example 57

Synthesis of Ru Complex 6f

The synthetic procedure is the same as in Example 52 in 1.0 mmol scale. 664 mg of yellow-green solid product 6f was obtained (17% yield).

Ru complex (6f) $^1$HNMR (400 MHz, CDCl$_3$): δ 18.60 (s, 1H, Ru=CH), 8.58 (s, 1H), 7.48-7.29 (m, 2H), 7.02 (d, J=8.8 Hz, 2H), 6.74-6.69 (m, 3H), 4.17 (s, 4H, NCH$_2$CH$_2$N), 3.85 (s, 3H), 2.52 (m, 18H).

Example 58

Synthesis of Ru Complex 6g

The synthetic procedure is the same as in Example 52 in 1.0 mmol scale. 35 mg of green solid product 6g was obtained (22% yield).

Ru complex (6g) $^1$H-NMR (400 MHz, CDCl$_3$): δ 18.66 (s, 1H, Ru=CH), 8.56 (s, 1H), 7.50-7.34 (m, 2H), 7.26 (s, 4H), 7.00-6.40 (m, 5H), 4.14 (s, 4H, NCH$_2$CH$_2$N), 3.81 (s, 3H), 2.49 (m, 18H).

Example 59

Synthesis of Ru Complex 6h

The synthetic procedure is the same as in Example 52 in 1.0 mmol scale. 106 mg of yellow-green solid product 6h was obtained (37% yield).

Ru complex (6h) $^1$HNMR (400 MHz, CDCl$_3$): δ 16.52 (s, 1H, Ru=CH), 8.43 (s, 1H, N=CH), 8.10 (s, 1H), 7.46-7.22 (m, 2H), 7.73-6.96 (m, 8H), 4.19 (s, 4H, NCH$_2$CH$_2$N), 3.95 (s, 3H), 3.87 (s, 3H), 2.49 (s, 12H), 2.48 (s, 6H).

Example 60

Synthesis of Ru Complex 6j

To a 50 mL two-necked round bottom flask, after filling with Ar atmosphere, were added ligand 5j (1.0 mmol) and CuCl (3.0 mmol, 3 eq) and 30 mL dry DCM, followed by refilling with Ar three times and protected with Ar balloon in close system. Ru complex 1a (1.0 mmol) was added under Ar protection, and the mixture was stirred for 0.5 hr at room temperature.

After the reaction was complete, the solution was filtered and the filtrate was concentrated and slurred with silica gel. The crude was obtained by silica gel column chromatography and washed with methanol or pentane-DCM to obtain 190 mg of red solid product 6j. The product is unstable. It is difficult to detect the structure by $^1$HNMR. But the crude Ru complex 6j could be directly used for metathesis reaction.

Example 61

Synthesis of Ru Complex 8a

The synthetic procedure is the same as in Example 1 in 1.0 mmol scale. 208 mg of green solid product 8a was obtained, yield: 32%.

Ru complex (8a) $^1$HNMR (400 MHz, CDCl$_3$): δ16.80 (s, 1H, Ru=CH), 7.07 (s, 4H, aromatic H), 6.94 (m, 1H), 6.30 (d, J=6.4 Hz, 1H), 4.11 (s, 4H, NCH$_2$CH$_2$N), 2.69 (s, 6H), 2.49 (s, (s, 12H), 2.42 (s, 6H).

Example 62

Synthesis of Ru Complex 8b

The synthetic procedure is the same as in Example 1 in 1.0 mmol scale. 59 mg of green solid product 8b was obtained (yield: 9%).

Ru complex (8b) $^1$HNMR (400 MHz, CDCl$_3$): δ 16.97 (s, 1H, Ru=CH), 8.40 (dd, J=8.8, 2.4 Hz, 1H), 7.65 (d, J=2.4 Hz, 1H), 7.29 (d, J=8.8 Hz, 1H), 7.07 (s, 4H), 4.20 (s, 4H, NCH$_2$CH$_2$N), 2.57 (s, 6H), 2.47 (s, 12H), 2.39 (s, 6H).

Example 63

Synthesis of Ru Complex 8c

The synthetic procedure is the same as in Example 1 in 1.0 mmol scale. 161 mg of green solid product 8c was obtained (24% yield).

Ru complex (8c) $^1$HNMR (400 MHz, CDCl$_3$): δ 16.69 (s, 1H, Ru=CH), 8.36 (dd, J=8.8, 2.4 Hz, 1H), 7.62 (d, J=2.4 Hz, 1H), 7.18 (d, J=8.8 Hz, 1H), 7.17-7.00 (m, 4H), 4.16-3.80 (m, 6H), 2.84-2.08 (m, 21H), 0.57 (t, J=6.8 Hz, 3H).

Example 64

Synthesis of Ru Complex 8d

The synthetic procedure is the same as in Example 1 in 1.0 mmol scale. 103 mg green solid product 8d was obtained, yield: 15%. The product is unstable, so it is difficult to detect the structure by $^1$HNMR. But the crude Ru complex 6j could be directly used for metathesis reaction.

Example 65

Synthesis of Ru Complex 8e

The synthetic procedure is the same as in Example 1 in 1.0 mmol scale. 74 mg green solid product 8d was obtained, yield: 15%. The product is unstable, so it is difficult to detect the structure by $^1$HNMR. But the crude Ru complex 6j could be directly used for metathesis reaction.

Example 66

Synthesis of Ru Complex 8f

The synthetic procedure is the same as in Example 1 in 1.0 mmol scale. 396 mg of green solid product 8f was obtained (yield: 59%).

Ru complex (8f) $^1$HNMR (400 MHz, CDCl$_3$): δ16.80 (s, 1H, Ru=CH), 8.18 (dd, J=8.8, 2.4 Hz, 1H), 7.46 (d, J=2.4 Hz, 1H), 7.23 (d, J=8.8 Hz, 1H), 7.07 (s, 4H), 4.11 (s, 4H, NCH$_2$CH$_2$N), 3.91 (s, 3H), 2.58 (s, 6H), 2.47 (s, 12H), 2.43 (s, 6H).

Example 67

Synthesis of Ru Complex 8g

The synthetic procedure is the same as in Example 1 in 1.0 mmol scale. 530 mg of green solid product 8g was obtained (yield: 79%).

Ru complex (8g) $^1$HNMR (400 MHz, CDCl$_3$): δ 16.70 (s, 1H, Ru=CH), 7.37 (m, 1H), 7.04-6.91 (m, 6H), 6.72 (d, J=7.6 Hz, 1H), 5.05 (d, J=11.6 Hz, 1H), 3.88-3.85 (m, 4H, NCH$_2$CH$_2$N), 3.52 (s, 3H), 3.44 (d, J=11.6 Hz, 1H), 2.85-1.50 (m, 21H).

Example 68

Synthesis of Ru Complex 8h

The synthetic procedure is the same as in Example 1 in 1.0 mmol scale. 530 mg of green solid product 8h was obtained (yield: 74%).

Ru complex (8h) $^1$HNMR (400 MHz, CDCl$_3$): δ 16.56 (s, 1H, Ru=CH), 8.33 (dd, J=8.4, 2.4 Hz, 1H), 7.56 (d, J=2.4 Hz), 7.20-6.94 (m, 5H), 5.22 (d, J=11.2 Hz, 1H), 4.21-3.96 (m, 4H, NCH$_2$CH$_2$N), 3.56 (s, 3H), 3.54 (d, J=11.2 Hz, 1H), 2.94-0.92 (m, 21H).

Example 69

Synthesis of Ru Complex 8j

The synthetic procedure is the same as in Example 1 in 1.0 mmol scale. 320 mg of green solid product 8j was obtained (yield: 43%).

Ru complex (8j) $^1$HNMR (400 MHz, CDCl$_3$): δ 16.64 (s, 1H, Ru=CH), 8.34 (dd, J=8.4, 2.4 Hz, 1H), 7.54 (d, J=2.4 Hz, 1H), 7.25-6.93 (m, 5H), 5.17 (d, J=11.2 Hz, 1H), 4.84-4.83 (m, 1H), 4.14-3.93 (m, 4H, NCH$_2$CH$_2$N), 3.45 (d, J=11.2 Hz, 1H), 2.89-1.19 (m, 27H).

Example 70

Synthesis of Ru Complex 8k

The synthetic procedure is the same as in Example 1 in 1.0 mmol scale. 530 mg of green solid product 8k was obtained (yield: 74%).

Ru complex (8k) $^1$HNMR (400 MHz, CDCl$_3$): δ 16.70 (s, 1H, Ru=CH), 7.18-7.13 (m, 3H), 7.05 (s, 1H), 6.96-6.94 (m, 2H), 6.48-6.45 (dd, J=8.0, 2.0 Hz, 1H), 5.19-5.16 (d, J=15.5 Hz, 1H), 4.17 (s, 2H), 3.94 (s, 2H), 3.62 (s, 3H), 3.50-3.47 (d, J=15.5 Hz, 1H), 2.94 (s, 3H), 2.80 (s, 3H), 2.49 (s, 3H), 2.32 (s, 6H), 2.00 (s, 6H).

Example 71

Synthesis of Ru Complex 8m

The synthetic procedure is the same as in Example 1 in 1.0 mmol scale. 430 mg of green solid product 8m was obtained (yield: 41%).

Ru complex (8m) $^1$HNMR (400 MHz, CDCl$_3$): δ 16.67 (s, 1H, Ru=CH), 7.10-7.16 (m, 3H), 7.02 (s, 1H), 6.91-6.94 (m, 2H), 6.43-6.45 (dd, J=8.75, 2.5 Hz, 1H), 5.13-5.16 (d, J=15.5

Hz, 1H), 4.15 (s, 2H), 3.91 (s, 2H), 3.59 (s, 3H), 3.44-3.47 (d, J=15.0 Hz, 1H), 2.92 (s, 3H), 2.77 (s, 3H), 2.47 (s, 3H), 2.29 (s, 6H), 1.97 (s, 6H).

Example 72

Synthesis of Ru Complex 8n

The synthetic procedure is the same as in Example 1 in 1.0 mmol scale. 599 mg of green solid product 8n was obtained (yield: 87%).

Ru complex (8n) $^1$HNMR (400 MHz, CDCl$_3$): δ16.82 (s, 1H, Ru=CH), 7.12-7.02 (m, 5H), 6.64 (m, 1H), 6.51-6.48 (m, 1H), 4.15 (s, 4H, NCH$_2$CH$_2$N), 3.95-3.92 (m, 1H), 3.74 (s, 3H), 2.50-2.37 (m, 18H), 0.96 (d, J=6.4 Hz, 1H).

Example 73

Synthesis of Ru Complex 8p

The synthetic procedure is the same as in Example 1 in 1.0 mmol scale. 379 mg of green solid product 8p was obtained (yield: 48%).

Ru complex (8p) $^1$HNMR (400 MHz, CDCl$_3$): δ17.58 (d, J=6.0 Hz, 1H, Ru=CH), 7.59-7.55 (m, 2H), 7.48 (d, J=8.4 Hz, 1H), 7.22 (dd, J=2.4, 8.8 Hz, 1H), 7.14 (d, J=8.4 Hz, 1H), 6.78 (d, J=8.8 Hz, 1H), 4.80 (d, J=12.8 Hz, 1H), 4.50-4.47 (m, 1H), 4.05 (d, J=12.8 Hz, 1H), 2.704 (s, 3H), 2.38-0.78 (m, 39H, PCy$_3$).

Example 74

Synthesis of Ru Complex 8q

The synthetic procedure is the same as in Example 1 in 1.0 mmol scale. 602 mg of green solid product 8q was obtained (yield: 77%).

Ru complex (8q) $^1$HNMR (400 MHz, CDCl$_3$): δ16.87 (s, 1H, Ru=CH), 7.41 (dd, J=2, 8.4 Hz, 1H), 7.19-7.13 (m, 5H), 7.031 (d, J=8.4 Hz, 1H), 6.93 (d, J=7.2 Hz, 1H), 6.77-6.76 (m, 2H), 6.65 (t, J=7.2 Hz, 1H), 4.66 (d, J=12.4 Hz, 1H), 4.48-4.43 (m, 1H), 4.02-3.98 (m, 5H), 2.54-2.30 (m, 18H), 2.25 (s, 3H), 1.29 (d, J=6 Hz, 6H).

Example 75

Synthesis of Ru Complex 8r

The synthetic procedure is the same as in Example 1 in 1.0 mmol scale. 302 mg of green solid product 8r was obtained (yield: 37%).

Ru complex (8r) $^1$HNMR (400 MHz, CDCl$_3$): δ16.84 (s, 1H, Ru=CH), 7.18 (d, J=8.4 Hz, 1H), 7.81 (m, 5H), 6.75 (m, 1H), 6.62 (d, J=8.8 Hz, 1H), 6.32 (d, J=8.4 Hz, 1H), 4.29-4.24 (m, 1H), 4.11 (s, 4H, NCH$_2$CH$_2$N), 3.85 (d, J=14.0 Hz, 1H), 3.09 (d, J=14.0 Hz, 1H), 2.74 (s, 3H), 2.43-2.28 (m, 18H), 1.10 (d, J=6.0 Hz, 6H).

Example 76

Synthesis of Ru Complex 10a

The synthetic procedure is the same as in Example 1 in 1.0 mmol scale. 128 mg of green solid product 10a was obtained (yield: 19%). The product is unstable, so it is difficult to detect the structure by $^1$HNMR. But the crude Ru complex 10a could be directly used for metathesis reaction.

Example 77

Synthesis of Ru Complex 10b

The synthetic procedure is the same as in Example 1 in 1.0 mmol scale. 97 mg of green solid product 10b was obtained (yield: 15%). The product is unstable, so it is difficult to detect the structure by $^1$HNMR. But the crude Ru complex 10b could be directly used for metathesis reaction.

Example 78

Synthesis of Ru Complex 10c

The synthetic procedure is the same as in Example 1 in 1.0 mmol scale. 29 mg of green solid product 10c was obtained (yield: 5%).

Ru complex (10c) $^1$HNMR (400 MHz, CDCl$_3$): δ 18.68 (s, 1H, Ru=CH), 8.44 (dd, J=8.4, 2.4 Hz, 1H), 8.20 (d, J=8.4 Hz, 1H), 7.60 (d, J=2.4 Hz, 1H), 7.13 (s, 4H), 4.14 (s, 4H, NCH$_2$CH$_2$N), 3.97 (s, 3H), 2.48 (s, 12H), 2.459 (s, 6H).

Example 79

Synthesis of Ru Complex 10d

The synthetic procedure is the same as in Example 1 in 1.0 mmol scale. 238 mg of green solid product 10d was obtained (yield: 34%).

Ru complex (10d) $^1$HNMR (400 MHz, CDCl$_3$): δ 18.71 (s, 1H, Ru=CH), 8.42 (dd, J=9.0, 2.4 Hz, 1H), 8.18 (d, J=9.0 Hz, 1H), 7.60 (d, J=2.4 Hz, 1H), 7.13 (s, 4H), 5.25 (m, 1H), 4.13 (s, 4H, NCH$_2$CH$_2$N), 2.46 (m, 18H), 1.24 (d, J=6.0 Hz, 6H).

Example 80

Synthesis of Ru Complex 10e

The synthetic procedure is the same as in Example 1 in 1.0 mmol scale. 235 mg of green solid product 10e was obtained (yield: 34%).

Ru complex (10e) $^1$HNMR (400 MHz, CDCl$_3$): δ 18.56 (s, 1H, Ru=CH), 7.98 (d, J=8.8 Hz, 1H), 8.18 (dd, J=8.8, 2.4 Hz, 1H), 7.11 (s, 4H), 7.06 (d, J=2.4 Hz, 1H), 5.23 (m, 1H), 4.11 (s, 4H, NCH$_2$CH$_2$N), 2.45 (m, 18H), 1.28 (d, J=6.0 Hz, 6H).

Example 81

Synthesis of Ru Complex 10f

The synthetic procedure is the same as in Example 1 in 1.0 mmol scale. 274 mg of green solid product 10f was obtained (yield: 37%).

Ru complex (10f) $^1$HNMR (400 MHz, CDCl$_3$): $^1$H-NMR (400 MHz, CDCl$_3$): δ 18.74 (s, 1H, Ru=CH), 8.21 (dd, J=8.0, 2.4 Hz, 1H), 8.08 (d, J=8.0 Hz, 1H), 7.54 (d, J=2.4 Hz, 1H), 7.12 (s, 4H), 5.32 (m, 1H), 5.25 (m, 1H), 4.13 (s, 4H, NCH$_2$CH$_2$N), 2.47 (m, 18H), 1.43 (d, J=6.0 Hz), 1.24 (d, J=6.0 Hz, 6H).

Example 82

Synthesis of Ru Complex 10g

The synthetic procedure is the same as in Example 1 in 1.0 mmol scale. 440 mg of green solid product 10g was obtained (yield: 53%).

Ru complex (10g) $^1$HNMR (400 MHz, CDCl$_3$): δ 18.60 (s, 1H, Ru=CH), 8.01 (d, J=8.4 Hz, 1H), 7.59 (dd, J=1.6, 8.4 Hz, 1H), 7.31-7.23 (m, 1H), 7.24 (dd, J=2.8, 8.8 Hz, 1H), 6.81 (d, J=8.8 Hz, 1H), 6.71 (d, J=2.0 Hz, 1H), 5.33 (s, 2H), 4.52 (m, 1H), 4.16 (s, 4H, NCH$_2$CH$_2$N), 2.51 (s, 12H), 2.48 (s, 6H), 1.28 (d, 6H, J=6.0 Hz).

Example 83

Synthesis of Ru Complex 10h

The synthetic procedure is the same as in Example 1 in 1.0 mmol scale. 183 mg of green solid product 10g was obtained (yield: 23%).

Ru complex (10g) $^1$HNMR (400 MHz, CDCl$_3$): δ 18.60 (s, 1H, Ru=CH), 8.00 (d, J=8.8 Hz, 1H), 7.55 (d, J=8.4 Hz, 1H), 7.32-7.29 (m, 1H), 7.14 (s, 4H), 7.01-6.70 (m, 4H), 5.38 (s, 2H), 4.56 (m, 1H), 4.16 (s, 4H, NCH$_2$CH$_2$N), 2.71 (s, 12H), 2.52 (s, 6H), 1.32 (d, J=6.0 Hz, 6H).

Example 84

Synthesis of Ru Complex 10j

The synthetic procedure is the same as in Example 1 in 1.0 mmol scale. 345 mg of yellow solid product 10j was obtained (yield: 41%).

It is confirmed by Ru complex (10j) $^1$HNMR (400 MHz, CDCl$_3$): δ 18.75 (s, 1H, Ru=CH), 8.45 (dd, J=8.8, 1.6 Hz, 1H), 8.21 (d, J=8.8 Hz, 1H), 7.64 (d, J=1.6 Hz, 1H), 7.39-7.25 (m, 2H), 7.17 (s, 4H), 6.83 (d, J=8.8 Hz, 1H), 5.37 (s, 2H), 4.53 (m, 1H), 4.15 (s, 4H, NCH$_2$CH$_2$N), 2.51 (m, 18H), 1.40 (d, J=6.0 Hz, 6H).

Example 85

Synthesis of Ru Complex 11a

The Ru complex (Grela catalyst 2f, 1.0 mmol) and 4-chlorin pyridine ligand (10 mmol) were reacted directly to form another Ru complex 11a in 20 mL of anhydrous DCM in a 100 mL of three-neck flask filled with inert gas (Ar), and the reaction mixture was stirred for 0.5 hr at room temperature. After complete, 20 mL of pentane (−10° C.) was added into reaction solution, then filtered and washed with MeOH to obtain 747 mg of yellow-green solid product 11a, yield: 95%.

Ru complex (11a) $^1$HNMR (400 MHz, CDCl$_3$): δ 17.00 (s, 1H), 8.47-6.83 (m, 11H), 4.91 (m, 1H), 4.17 (s, 4H), 2.48-2.41 (m, 18H), 1.26 (d, J=4.4 Hz, 6H).

Example 86

Synthesis of Ru Complex 11b

The synthetic procedure is the same as in Example 85. 394 mg of yellow-green solid product 11b was obtained (yield: 48%).

Ru complex (11b) $^1$HNMR (400 MHz, CDCl$_3$): δ 16.49 (s, 1H), 8.90-8.50 (m, 2H), 7.86 (d, J=7.2 Hz, 1H), 7.47 (dd, J=2.0, 7.2 Hz, 1H), 7.33 (m, 1H), 7.27 (m, 1H), 7.08 (s, 3H), 6.90 (d, J=1.6 Hz, 1H), 6.74-6.72 (m, 1H), 4.87-4.84 (m, 1H), 4.19 (s, 4H), 2.48-2.42 (m, 18H), 1.27 (d, J=4.0 Hz, 6H).

Example 87

Synthesis of Ru Complex 11c

The synthetic procedure is the same as in Example 85. 733 mg of yellow-green solid product 11c was obtained (yield: 95%).

Ru complex (11e) $^1$HNMR (400 MHz, CDCl$_3$): δ 16.56 (s, 1H), 7.47 (dd, J=2.0, 7.2 Hz, 1H), 7.31-7.27 (m, 5H), 7.20-7.19 (m, 3H), 7.08-6.94 (m, 1H), 6.72 (d, J=6.4 Hz, 1H), 4.85-4.81 (m, 1H), 4.18 (s, 3H), 3.85 (s, 4H), 2.48-2.31 (m, 18H), 1.26 (d, J=6.0 Hz, 6H).

Example 88

Synthesis of Ru Complex 11d

The synthetic procedure is the same as in Example 85. 403 mg of yellow-green solid product 11d was obtained (yield: 52%).

Ru complex (11d) $^1$HNMR (400 MHz, CDCl$_3$): δ 16.49 (s, 1H), 8.67 (m, 2H), 7.47 (d, J=5.6 Hz, 1H), 7.37 (m, 3H), 7.08 (s, 3H), 6.73 (d, J=6.8 Hz, 1H), 4.85-4.83 (m, 1H), 4.19 (s, 4H), 2.48-2.41 (m, 18H), 1.26 (d, J=4.4 Hz, 6H).

Example 89

Synthesis of Ru Complex 11e

The synthetic procedure is the same as in Example 85. 458 mg of yellow-green solid product 11e was obtained (yield: 59%).

It is confirmed by Ru complex (11e) $^1$HNMR (400 MHz, CDCl$_3$): δ 16.52 (s, 1H), 8.60-8.51 (m, 2H), 7.67 (d, J=8.0 Hz, 2H), 7.46 (d, J=2.4 Hz, 1H), 7.06 (s, 4H), 6.88 (d, J=2.4 Hz, 1H), 6.71 (d, J=8.0 Hz, 2H), 4.84-4.81 (m, 1H), 4.16 (s, 4H), 2.45-2.39 (m, 18H), 1.24 (d, J=4.0 Hz, 6H).

Example 90

Synthesis of Ru Complex 11f

The synthetic procedure is the same as in Example 85. 733 mg of yellow-green solid product 11f was obtained (yield: 97%).

Ru complex (11f) $^1$HNMR (400 MHz, CDCl$_3$): δ 16.57 (s, 1H), 7.63-6.69 (m, 11H), 4.83-4.81 (m, 1H), 4.16 (s, 4H), 2.45-2.39 (m, 21H), 1.24 (d, J=4.0 Hz, 6H).

Example 91

Synthesis of Ru Complex 11g

The synthetic procedure is the same as in Example 85. 330 mg of yellow-green solid product 11g was obtained (yield: 37%).

Ru complex (11g) $^1$HNMR (400 MHz, CDCl$_3$): δ 18.67 (s, 1H), 8.40 (m, 1H), 7.47-6.91 (m, 13H), 6.58 (m, 1H), 4.12 (m, 6H), 2.63-2.27 (m, 19H), 1.00 (d, J=4.0 Hz, 6H).

Example 92

Synthesis of Ru Complex 11h

The synthetic procedure is the same as in Example 85. 619 mg of yellow-green solid product 11h was obtained (yield: 73%).

Ru complex (11h) $^1$HNMR (400 MHz, CDCl$_3$): δ 18.67 (s, 1H), 8.43 (s, 1H), 7.45-7.35 (m, 3H), 7.19-6.93 (m, 10H), 6.60 (d, J=7.6 Hz, 1H), 4.15 (m, 6H), 2.52-2.28 (m, 19H), 1.08-0.89 (m, 6H).

Example 93

Synthesis of Ru Complex 11j

The synthetic procedure is the same as in Example 85. 416 mg of yellow-green solid product 11j was obtained (yield: 49%).
Ru complex (11j) $^1$HNMR (400 MHz, CDCl$_3$): δ 18.67 (s, 1H), 8.40 (m, 1H), 7.69-6.90 (m, 13H), 6.60 (m, 1H), 4.12 (m, 6H), 2.62-2.17 (m, 19H), 1.00 (d, J=4.0 Hz, 6H).

Example 94

Synthesis of Ru Complex 11k

The synthetic procedure is the same as in Example 85. 561 mg of yellow-green solid product 11k was obtained (yield: 63%).
Ru complex (11k) $^1$HNMR (400 MHz, CDCl$_3$): δ18.69 (s, 1H), 8.42 (s, 2H), 7.62-6.93 (m, 16H), 6.60 (dd, J=2.0, 7.6 Hz, 2H), 4.14 (s, 6H), 2.52-2.27 (m, 18H), 0.98 (d, J=4.4 Hz, 6H).

Example 95

Synthesis of Ru Complex 11m

The synthetic procedure is the same as in Example 85. 685 mg of yellow-green solid product 11m was obtained (yield: 78%).
Ru complex (11m): $^1$H-NMR (400 MHz, CDCl$_3$): δ 16.85 (s, 1H), 8.42-7.07 (m, 15H), 4.95 (m, 1H), 4.19 (s, 4H), 2.45-2.29 (m, 18H), 1.29 (d, J=4.4 Hz, 6H).

Example 96

Synthesis of Ru Complex 11n

The synthetic procedure is the same as in Example 85. 704 mg of yellow-green solid product 11n was obtained (yield: 85%).
Ru complex (11n) $^1$HNMR (400 MHz, CDCl$_3$): δ416.85 (s, 1H), 8.47-6.85 (m, 16H), 4.94 (m, 1H), 4.19 (s, 4H), 2.40-2.29 (m, 18H), 1.29 (d, J=4.4 Hz, 6H).

Example 97

Synthesis of Ru Complex 11p

The synthetic procedure is the same as in Example 85. 797 mg of yellow-green solid product 11p was obtained (yield: 96%).
Ru complex (11p) $^1$HNMR (400 MHz, CDCl$_3$): δ17.00 (s, 1H), 8.47-6.82 (m, 11H), 4.90 (m, 1H), 4.17 (s, 4H), 2.48-2.41 (m, 18H), 1.26 (d, J=4.4 Hz, 6H).

Example 98

Synthesis of Ru Complex 11q

The synthetic procedure is the same as in Example 85. 365 mg of yellow-green solid product 11q was obtained (yield: 47%).

Ru complex (11q) $^1$HNMR (400 MHz, CDCl$_3$): δ 17.33 (s, 1H), 8.71 (s, 1H), 8.56 (d, J=3.2 Hz, 1H), 7.84 (d, J=6.0 Hz, 1H), 7.41-7.34 (m, 1H), 7.23-7.21 (m, 1H), 7.01 (dd, J=3.2, 9.6 Hz), 5.23-5.21 (m, 1H), 2.37-0.90 (m, 33H).

Example 99

Synthesis of Ru Complex 11r

The synthetic procedure is the same as in Example 85. 604 mg of yellow-green solid product 11r was obtained (yield: 69%).
Ru complex (11r) $^1$HNMR (400 MHz, CDCl$_3$): δ 18.65 (s, 1H), 8.56 (s, 1H), 7.50-6.39 (m, 20H), 4.14 (s, 4H), 3.80 (s, 3H), 2.42-2.29 (m, 18H).

Example 100

Synthesis of Ru Complex 41

Starting material 4-SM (44 g, 100 mmol) and anhydrous ethanol (250 mL) were added into a 500 mL three-necked flask filled with inert gas (Ar), followed by adding NaOEt (400 mmol, 4.0 eq) was quickly added with agitation. The reaction mixture was heated to 60° C. After the reaction was completed in 0.5-1.0 hr, 120 mL of water was added into flask, and the aqueous layer was extracted with pentane (200 mL×3), and the combined organic layers were washed with brine (150 mL×2) solution, then dried over NaSO$_4$ and concentrated to obtain about 50 mL of crude carbine intermediate 4-1 directly for next step at 0-5° C.

RuCl$_2$(PPh$_3$)$_3$ (29 g, 30 mmol) was dissolved in 250 mL of anhydrous DCM in a 500 mL three-neck flask filled with inert gas (Ar), and the DCM solution was cooled to –70° C., then the previously prepared crude carbine intermediate 4-1 (50 mL) was added into the DCM solution at –70° C. After 10 min, the solution was heated to room temperature, and CuCl (100 mmol) was added. After completed in 30 min, the reaction solution was filtered and purified by silica gel column chromatography (eluting solution: n-hexane:DCM=2:1 to pure DCM). The product was concentrated and washed by anhydrous n-hexane. After dried by vacuum, the Ru complex intermediate 4-2 (19.3 g) was obtained.

The intermediate 4-2 (10.0 mmol) and tricyclohexylphosphine (PCy$_3$, 20 mmol, 2.0 eq.) were dissolved in DCM (30 mL) in a 250 mL three-neck flask filled with inert gas (Ar), then stirred at 20° C. for about 30 min. After completed, the crude product was purified by flash column to obtain dark-green solid. The solid product was washed with anhydrous methanol and n-hexane to obtain green solid product 4i (crude yield: 60-70%). The product 4i is not stable and difficult to analyze the structure by $^1$HNMR. But the crud Ru complex 4i can be used directly to prepare 4j in next step.

Example 101

Synthesis of Ru Complex 4j

The Ru complex 4i (5.0 mmol) and a ligand H$_2$IMes(H) (CCl$_3$) (4-4, 10.0 mmol, 2.0 eq.) were dissolved in anhydrous toluene (30 mL) in a 100 mL two-necked flask filled with Ar gas. The reaction mixture was heated to 80° C. for 1.5 hr. After the reaction was completed, the solution was cooled and filtered, then purified by flash column to obtain dark-green product. The crude product was washed by methanol and pentane-DCM to offer 2.3 g of stable green solid product 4j (yield: 59%).

Ru complex 4j is confirmed by $^1$HNMR (400 MHz, CDCl$_3$): δ 18.88 (s, 1H, Ru=CH), 7.57-6.44 (m, 11H, aromatic H), 5.36 (t, J=13.2 Hz, 1H, NH), 4.16-4.02 (m, 5H, NCH$_2$, NCH$_2$CH$_2$N), 4.01 (d, J=13.2 Hz, 1H, NCH$_2$), 2.75-2.00 (m, 19H, CH(CH$_3$)$_2$, aromatic CH$_3$), 1.01-0.90 (m, 6H, CH(CH$_3$)$_2$).

Example 102

Synthesis of Ru Complex 11h

The Ru complex 4j (0.2 mmol) and 4-chlorin pyridine 4-chlorin pyridine ligand (4-5, 2.0 mmol) were reacted directly to form another Ru complex 11h in 10 mL of anhydrous DCM in a 100 mL three-neck flask filled with inert gas (Ar). Preparation method and result of the Ru complex 11h was the same as described in Example 92. 619 mg of yellow-green solid product 11h was obtained (yield: 73%).

Ru complex 11h is confirmed by $^1$HNMR (400 MHz, CDCl$_3$): δ 18.67 (s, 1H), 8.43 (s, 1H), 7.45-7.35 (m, 3H), 7.19-6.93 (m, 10H), 6.60 (d, J=7.6 Hz, 1H), 4.15 (m, 6H), 2.52-2.28 (m, 19H), 1.08-0.89 (m, 6H).

Example 103

Synthesis of Ru Complex 6h

The Ru complex (Zhan catalyst 2b, 1.0 mmol) and a new ligand 5h (1.5 mmol) were dissolved in 20 mL of anhydrous DCM and reacted directly to form the desired Ru complex 6h in the presence of CuCl (3.0 mmol) in a 100 mL of three-neck flask filled with inert gas (Ar). The reaction mixture was stirred for 0.5 hr at room temperature. After complete, the reaction solution was filtered and purified by flask column. 378 mg of yellow-green solid product 6h was obtained, yield: 52%.

Ru complex 6h is confirmed by $^1$HNMR (400 MHz, CDCl$_3$): δ 16.52 (s, 1H, Ru=CH), 8.43 (s, 1H, N=CH), 8.10 (s, 1H), 7.46-7.22 (m, 2H), 7.73-6.96 (m, 8H), 4.19 (s, 4H, NCH$_2$CH$_2$N), 3.95 (s, 3H), 3.87 (s, 3H), 2.49 (s, 12H), 2.48 (s, 6H).

Example 104

Catalyst Screening for RCM Reaction

RCM Test by Selecting the Ru Complexes of Examples 1-103 as Catalyst

General Procedure for RCM Catalyzed by Ru Complex in DCM: Olefin substrate (15 or 17, 50 mg/each, respectivrly) was dissolved in 1.0 mL of freshly distilled DCM in a 15 mL two-neck round-bottom flask under Ar at 20-25° C., then Ru catalyst (2 mol % of Ru complex selected from Examples 1-103, respectively) was added into the DCM solution. The kinetic data for conversion of RCM reactions in Equations 1-2 were determined by HPLC at 10 min., 30 min. 1.5 hr, 3.0 hr and until completed overnight. The RCM product (16 and 18, respectivrly) was determined and the conversion results of RCM reactions were listed in Tables 1-1, 1-2, 1-3, 1-4, 1-5, and 2 above, respectively.

The RCM product 16 is confirmed by $^1$HNMR (400 MHz, CDCl$_3$): δ 7.72 (d, J=8.2 Hz, 1H), 7.32 (d, J=8.0 Hz, 1H), 5.66 (d, J=4.4 Hz, 1H), 4.11 (d, J=4.4 Hz, 1H), 2.42 (s, 3H). m/z calculated: 222.1. found: 222.2.

The RCM product 18 is confirmed by $^1$HNMR (400 MHz, CDCl$_3$): δ 7.78 (d, 2H, J=8.21 Hz), 7.31 (m, 7H), 6.01 (m, 1H), 4.47 (m, 2H), 4.30 (m, 2H), 2.41 (s, 3H). (M+H$^+$): m/z calculated: 300.1. found: 300.2.

Example 105

Catalyst Screening for Cross Metathesis Reaction

CM Test by Selecting the Ru Complexes of Examples 1-103 as Catalyst

General Procedure for CM Catalyzed by Ru Complex in DCM: Olefin substrate (19, 200 mg/each, respectivrly) was dissolved in 3.0 mL of freshly distilled DCM in a 15 mL two-neck round-bottom flask under Ar at 20-25° C., then Ru catalyst (0.1 mol % of Ru complex selected from Examples 1-103, respectively) was added into the DCM solution. The CM reaction results are described in section of Equation 3 above.

Example 106

Catalyst Screening for ROMP Reaction without Solvent

ROMP Test by Selecting the Ru Complexes of Examples 1-103 as Catalyst

General Procedure for ROMP Catalyzed by Ru Complex without solvent for some liquid olefin substrates: Olefin substrate (21, 23 or 25, 5 mL/each, respectivrly) was added into a 25 mL flat-bottom bottle under Ar at 40-50° C., then Ru catalyst (0.1 mol % of Ru complex selected from Examples 1-103, respectively) was added with agitation. The kinetic data and ROMP results for products 22, 24 and 26 are described in each section of Equation 4-6 above, respectively.

Example 107

Catalyst Screening for ROMP Reaction with Solvent

ROMP Test by Selecting the Ru Complexes of Examples 1-103 as Catalyst

General Procedure for ROMP Catalyzed by Ru Complex in solution: 0.5 g of cyclo-olefin substrate (21, 23, 25, 27, 29, or 31, respectivrly) was dissolved in 10 mL of freshly distilled DCM in a 25 mL two-neck round-bottom flask under Ar at 20-25° C., then Ru catalyst (0.1 mol % of Ru complex selected from Examples 1-103, respectively) was added into the DCM solution. The ROMP results for products 22, 24, 26, 28, 30 and 32 are described in each section of Equation 4-9 above, respectively.

What is claimed is:
1. A transition metal catalyst having the following structure Ia or Ib:

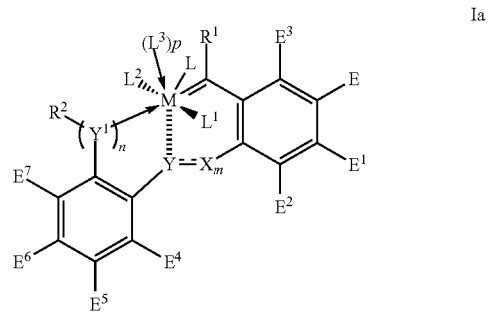

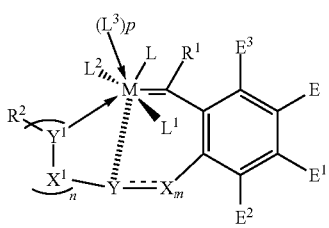

Ib wherein:

m=0 or 1, and n=1;

p=0;

M is a transition metal selected from ruthenium (Ru), molybdenum (Mo) or tungsten (W);

$L^1$ and $L^2$ are the same or different and each selected from halide anion, carboxylate or aryloxide anion;

L is an electron-donating ligand;

when m=1, X is nitrogen, sulfur, CH, $CH_2$, or carbonyl; Y is nitrogen, imino, alkylcarbonyl, alkoxycarbonyl, arylcarbonyl, aryloxycarbonyl, alkylimino, arylimino, alkylamino, arylamino or heterocyclic amino group;

"Y═X"

is either single bond or double bond when Y is nitrogen;

when m=0, Y is nitrogen, carbonyl, imino, alkoxycarbonyl, aryloxycarbonyl, alkylimino, arylimino, alkylamino, arylamino or heterocyclic amino group;

$X^1$ is a CH or $CH_2$ and $Y^1$ is oxygen, nitrogen, carbonyl, imino, heterocyclic aryl, alkylamino, arylamino or a heterocyclic amino group;

$R^1$ is H, alkyl, alkenyl, aryl, arylenyl, alkoxy, alkylthio, arylthio, aryloxy, heteroaryl or heterocyclic group;

$R^2$ is H, alkyl, aryl, alkylcarbonyl, arylcarbonyl heteroaryl or heterocyclic group;

E, $E^1$, $E^2$, $E^3$, $E^4$, $E^5$, $E^6$ and $E^7$ each is independently selected from the group consisting of H, halogen atom, nitro, amino, cyano, formyl, sulfinyl, sulfonyl, alkyl, alkoxy, alkylthio, alkylphosphino, alkenyloxy, silanyl, alkylsilyloxy, aryl, aryloxy, arylphosphino, alkylcarbonyl, arylcarbonyl, alkoxycarbonyl, aryloxycarbonyl, amino, alkylaminocarbonyl, arylaminocarbonyl, alkylamido, arylamido, alkylaminosulfonyl, arylaminosulfonyl, sulfonylamido, heteroaryl and heterocyclic group; each optionally unsubstituted or substituted with an alkyl, alkoxy, alkylthio, aryl, aryloxy, halogen atom or heterocyclic group; each of E, $E^1$, $E^2$ or $E^3$ may be linked with at least one other of E, $E^1$, $E^2$ or $E^3$ adjacent moiety to form a polycyclic-ligand via carbon-carbon and/or carbon-heteroatom bonds; and each of $E^4$, $E^5$, $E^6$ or $E^7$ may be linked with at least one other of $E^4$, $E^5$, $E^6$ or $E^7$ adjacent moiety to form a polycyclic-ligand via carbon-carbon and/or carbon-heteroatom bond.

2. The transition metal catalyst according to claim 1, wherein $L^1$ and $L^2$ each is a halide anion.

3. The transition metal catalyst according to claim 2, wherein $L^1$ and $L^2$ each is a chloride anion ($Cl^-$).

4. The transition metal catalyst according to claim 1, wherein L is an electron donating ligand selected from phosphine, amino, aryloxides, carboxylate; or heterocyclic carbene group, which may be linked to $L^1$ via carbon-carbon and/or carbon-heteroatom bonds.

5. The transition metal catalyst according to claim 4, wherein L is N-heterocyclic carbene ligand (NHC) or phosphine $P(R^8)_2(R^9)$ having the following structure IIa, IIb, IIc, or IId:

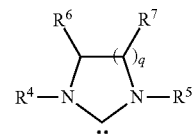

IIa

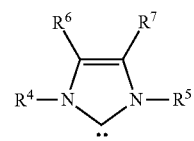

IIb

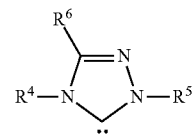

IIc

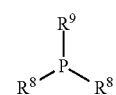

IId wherein:

q=1, 2 or 3;

$R^4$ and $R^5$ each is $C_{1-12}$ alkyl, $C_{6-12}$ aryl or $C_{3-12}$ heteroaryl; and $R^6$ and $R^7$ each is H, halogen, alkyl, alkoxy, aryl, aryloxy, alkylcarbonyl, arylcarbonyl, alkoxycarbonyl, aryloxycarbonyl, heteroaryl, carboxyl, cyano, nitro, amido, amino, alkylsulfonyl, arylsulfonyl, alkylsulfinyl, arylsulfinyl, alkylthio, arylthio, or sulfonamido group; and $R^8$ and $R^9$ each is $C_{1-12}$ alkyl or $C_{6-12}$ aryl group.

6. The transition metal catalyst according to claim 5, wherein q=1; L is IIa or IId, $R^4$ and $R^5$ each is 2,4,6-trimethylphenyl (mesityl), $R^6$ and $R^7$ each is H, and $R^8$ and $R^9$ each is cyclohexyl (Cy).

7. The transition metal catalyst according to claim 1, wherein $R^1$ is H.

8. The transition metal catalyst according to claim 1, wherein $R^2$ is H, alkyl, alkylcarbonyl or arylcarbonyl.

9. The transition metal catalyst according to claim 8, wherein $R^2$ is H, halogen, methyl, ethyl, isopropyl, $C_1$-$C_{12}$ alkyl, $C_1$-$C_{12}$ alkylcarbonyl or $C_6$-$C_{12}$ arylcarbonyl in structure Ia or Ib, respectively.

10. The transition metal catalyst according to claim 1, wherein:

when m=0, Y is nitrogen, carbonyl, alkoxycarbonyl, alkylimino, arylimino, alkylamino or arylamino group;

when m=1, X is CH, or CH$_2$; Y is nitrogen, alkoxycarbonyl, alkylamino or arylamino group;

"Y=X"

is either single bond or double bond when Y is nitrogen, when n=1, X$^1$ is CH, CH$_2$, alkyl or an aryl group and Y$^1$ is oxygen, nitrogen, carbonyl, aryloxy, alkylamino or arylamino group.

11. The transition metal catalyst according to claim 10, wherein:
when m=0, Y is nitrogen, carbonyl, C$_1$-C$_{12}$ alkylimino, C$_6$-C$_{12}$ arylimino, C$_1$-C$_{12}$ alkylamino or C$_6$-C$_{12}$ arylamino group;
when m=1, X is CH or CH$_2$; Y is nitrogen, C$_1$-C$_{12}$ alkoxycarbonyl, C$_1$-C$_{12}$ alkylamino or C$_6$-C$_{12}$ arylamino group;

"Y=X"

is either single bond or double bond when Y is a nitrogen atom;
Y$^1$ is oxygen, nitrogen, carbonyl, C$_1$-C$_{12}$ alkylamino or C$_6$-C$_{12}$ arylamino group.

12. The transition metal catalyst according to claim 1, wherein E, E$^1$, E$^2$, E$^3$, E$^4$, E$^5$, E$^6$, and E$^7$ are each independently selected from the group consisting of H, halogen atom, nitro, alkyl, alkoxy, alkylthio, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and a C$_2$-C$_8$ heterocyclic group; each optionally substituted with halogen atom, alkyl, alkoxy, alkylthio, aryl, aryloxy or heterocyclic group.

13. The transition metal catalyst according to claim 12, wherein E is H, halogen, nitro, C$_1$-C$_{12}$ alkyl, C$_1$-C$_{12}$ alkoxy, C$_1$-C$_{12}$ alkoxycarbonyl, C$_1$-C$_{12}$ alkylaminosulfonyl, C$_6$-C$_{12}$ arylaminosulfonyl; E$^1$ and E$^2$ each is H, halogen, C$_1$-C$_4$ alkyl or C$_1$-C$_4$ alkoxy; E$^3$ is H; E$^4$ is H or C$_1$-C$_{12}$ alkyl; E$^5$ and E$^6$ each is H, halogen, C$_1$-C$_{12}$ alkyl or C$_1$-C$_{12}$ alkoxy; E$^7$ is H or C$_1$-C$_{12}$ alkyl group.

14. The transition metal catalyst according to claim 1, wherein the transition metal is ruthenium (Ru).

15. A method of carrying out a metathesis reaction with olefin substrate, comprising intramolecular ring-closing metathesis (RCM), intermolecular cross metathesis (CM) or ring-opening metathesis polymerization (ROMP) of cycloolefin substrate in the presence of the catalyst of claim 1.

16. The method according to claim 15, wherein a cycloolefin substrate for ROMP is selected from cyclooctene, dicyclopentadiene (DCPD), or norbornene; each is optionally substituted or unsubstituted with one or more of halogen, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or heterocyclic group.

17. A method of making functional polymers, comprising reacting one or more monomers in the presence of one or two more mixed catalysts of claim 1.

* * * * *